US012662673B2

(12) United States Patent
Lim et al.

(10) Patent No.: US 12,662,673 B2
(45) Date of Patent: Jun. 23, 2026

(54) LIPOPROTEIN-MIMICKING SOLID LIPID NANOPARTICLES FOR DRUG DELIVERY AND USES THEREOF

(71) Applicant: TIONLAB THERAPEUTICS, Yongin-si (KR)

(72) Inventors: Duck Soo Lim, Suwon-si (KR); Jin-Ho Kim, Seoul (KR)

(73) Assignee: TIONLAB THERAPEUTICS, Yongin-si (KR)

( * ) Notice: Subject to any disclaimer, the term of this patent is extended or adjusted under 35 U.S.C. 154(b) by 515 days.

(21) Appl. No.: 18/018,986

(22) PCT Filed: May 23, 2022

(86) PCT No.: PCT/KR2022/007299
§ 371 (c)(1),
(2) Date: Jan. 31, 2023

(87) PCT Pub. No.: WO2022/255701
PCT Pub. Date: Dec. 8, 2022

(65) Prior Publication Data
US 2024/0117355 A1      Apr. 11, 2024

(30) Foreign Application Priority Data
Jun. 1, 2021    (KR) ........................ 10-2021-0070586

(51) Int. Cl.
| | |
|---|---|
| *C12N 15/113* | (2010.01) |
| *A61K 9/51* | (2006.01) |
| *A61K 31/337* | (2006.01) |
| *A61K 31/7105* | (2006.01) |
| *A61K 47/54* | (2017.01) |
| *A61K 47/64* | (2017.01) |
| *A61K 47/69* | (2017.01) |
| *A61P 35/00* | (2006.01) |

(52) U.S. Cl.
CPC ........ *C12N 15/1137* (2013.01); *A61K 9/5123* (2013.01); *A61K 31/337* (2013.01); *A61K 31/7105* (2013.01); *A61K 47/548* (2017.08); *A61K 47/554* (2017.08); *A61K 47/643* (2017.08); *A61K 47/6929* (2017.08); *A61P 35/00* (2018.01); *C12N 2310/14* (2013.01)

(58) Field of Classification Search
CPC .............. A61K 31/337; A61K 31/7105; A61K 47/6929; A61K 48/0041; A61K 31/713; A61P 35/00; C12N 2310/14; C12N 15/1135; C12N 2310/51; C12N 2320/32; C12N 15/88
See application file for complete search history.

(56) References Cited

U.S. PATENT DOCUMENTS

| | | | | |
|---|---|---|---|---|
| 8,734,853 B2 * | 5/2014 | Sood | ................. | A61K 48/0041 424/499 |
| 2014/0080897 A1 | 3/2014 | Hahn et al. | | |
| 2014/0094383 A1 | 4/2014 | Lee et al. | | |
| 2015/0297749 A1 * | 10/2015 | Hahn | ................... | A61K 9/1272 424/502 |
| 2022/0211633 A1 * | 7/2022 | Thaxton | ............... | A61K 47/543 |

FOREIGN PATENT DOCUMENTS

| | | | | |
|---|---|---|---|---|
| CA | 3127256 A1 * | 7/2020 | ........... | A61K 47/544 |
| CN | 107802508 A | 3/2018 | | |
| KR | 10-2010-0085079 A | 7/2010 | | |
| KR | 10-2013-0049668 A | 5/2013 | | |
| WO | 2009051451 A2 | 4/2009 | | |

OTHER PUBLICATIONS

Battogtokh et al., Long-circulating self-assembled cholesteryl albumin nanoparticles enhance tumor accumulation of hydrophobic anticancer drug. European Journal of Pharmaceutics and Biopharmaceutics 96 (2015) 96-105 (Year: 2015).*
Yu et al., Synthesis and Immunotropic Activity of a Conjugate of Cholesterol with Protein. Scientific-Research Institute for the Biological Testing of Chemical Compounds, Moscow Province. Translated from Khimiko-Farmatsevticheskii Zhurnal, vol. 12, No. 6, pp. 35-38, Jun. 1978. (Year: 1978).*
(Brown, High-density lipoprotein and transport of cholesterol and triglyceride in blood. Journal of Clinical Lipidology, vol. 1, No. 1, Mar. 2007 (Year: 2007).*
International Searching Authority (ISA/KR). International Search Report. PCT Application No. PCT/KR2022/007299. Issued on Aug. 31, 2022. 8 pages, including English translation.
Battogtokh, G. et al. Long-circulating self-assembled cholesteryl albumin nanoparticles enhance tumor accumulation of hydrophobic anticancer drug. European Journal of Pharmaceutics and Biopharmaceutics 96 (2015): 96-105.
Samowitz, Wade S. et al. Relationship of Ki-ras mutations in colon cancers to tumor location, stage, and survival: a population-based study. Cancer Epidemiology Biomarkers & Prevention 9.11 (2000): 1193-1197.
Extended European Search Report for European Application No. 22816360.6, dated Apr. 23, 2025, 10 Pages.

* cited by examiner

*Primary Examiner* — Robert A Wax
*Assistant Examiner* — Ngoc-Anh Thi Nguyen
(74) *Attorney, Agent, or Firm* — Meunier Carlin & Curfman LLC

(57) ABSTRACT

According to the present invention, it is possible to provide a drug carrier having excellent bioavailability and improved drug encapsulation efficiency by preparing lipoprotein-mimicking solid lipid nanoparticles having a core-shell structure consisting of albumin-conjugated cholesterol, a fusogenic lipid, a cationic lipid, a triglyceride and a cholesteryl ester.

20 Claims, 7 Drawing Sheets
Specification includes a Sequence Listing.

【Fig. 1】
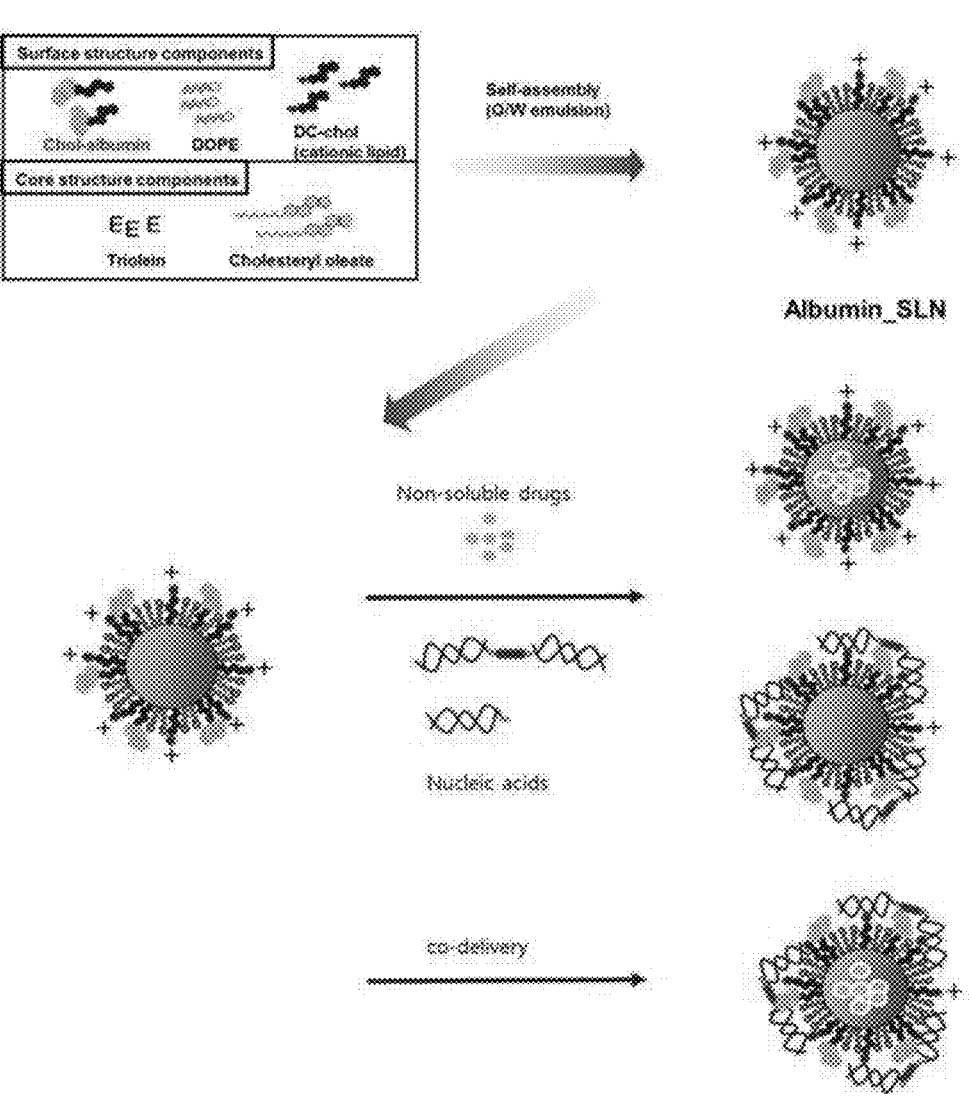

【Fig. 2】
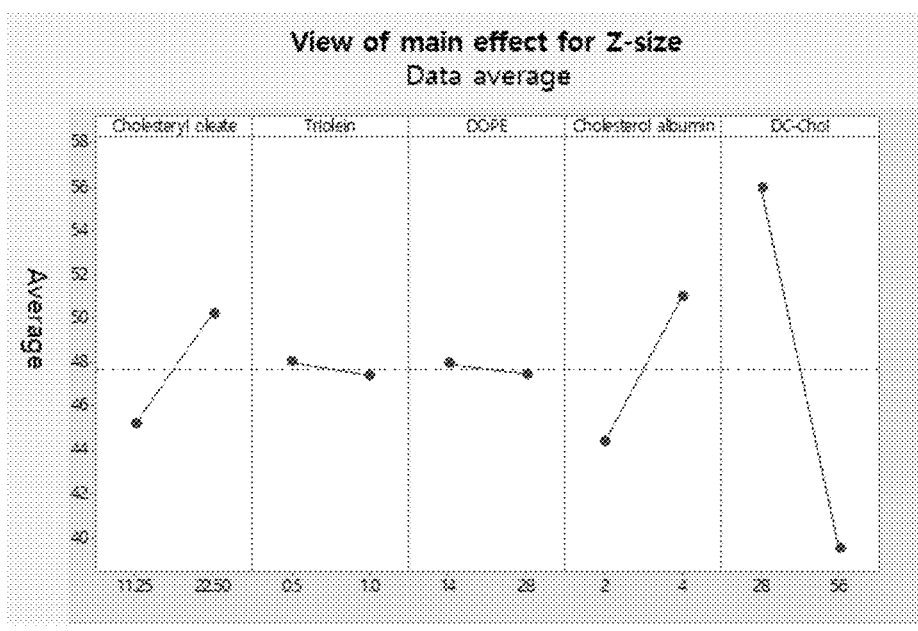
【Fig. 3A】
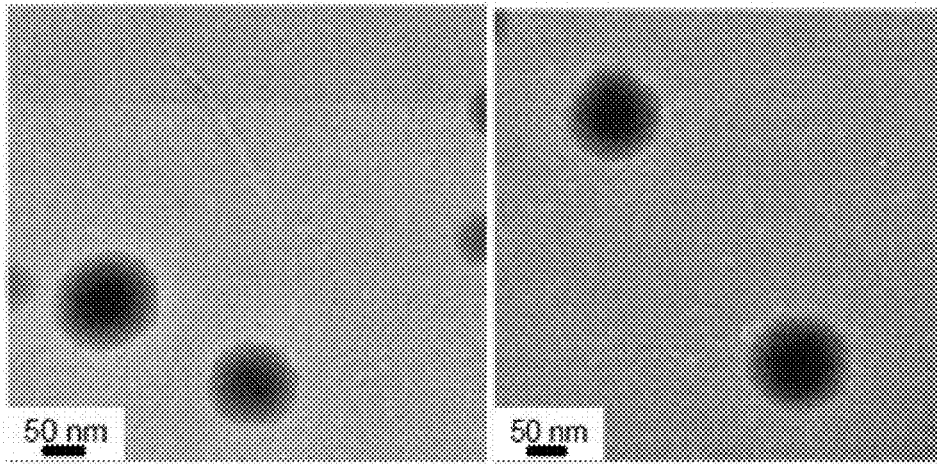

【Fig. 3B】
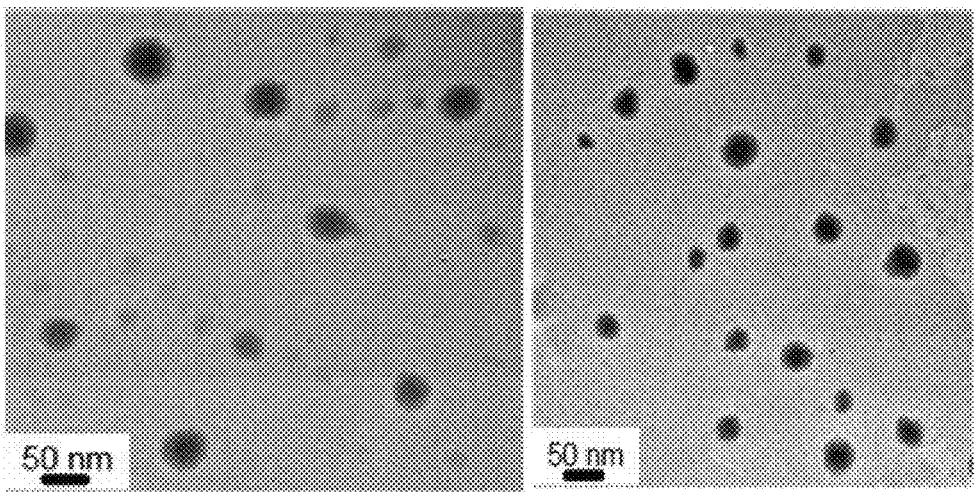
【Fig. 4】
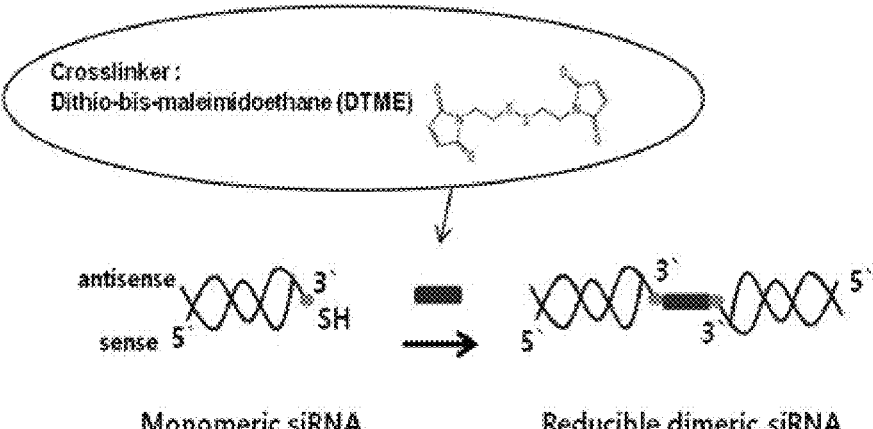

【Fig. 5】
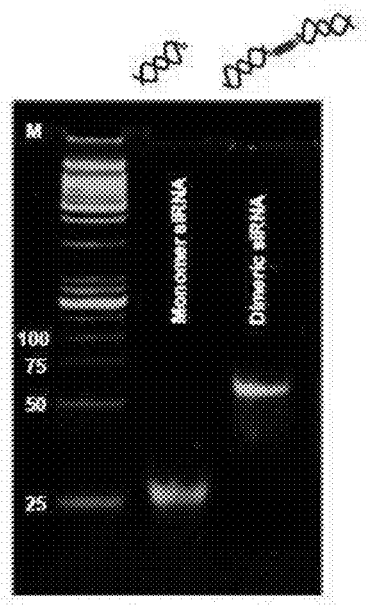
【Fig. 6】
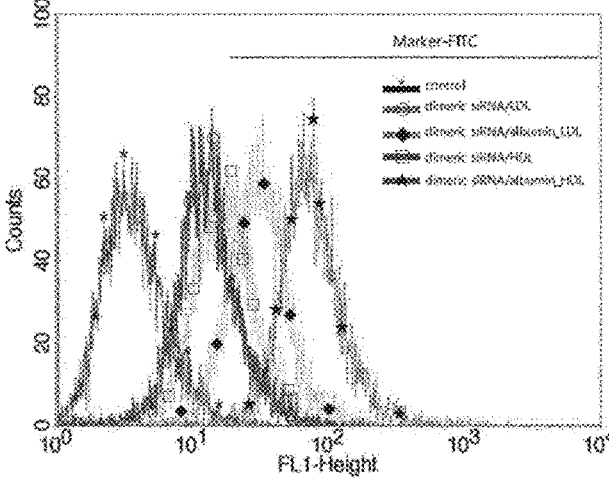
| siRNA formulations | % of marker region |
|---|---|
| dimeric siRNA/LDL | 14.26 |
| dimeric siRNA/albumin LDL | 73.58 |
| dimeric siRNA/HDL | 29.42 |
| dimeric siRNA/albumin HDL | 97.23 |

【Fig. 7】
Kras siRNA                control siRNA
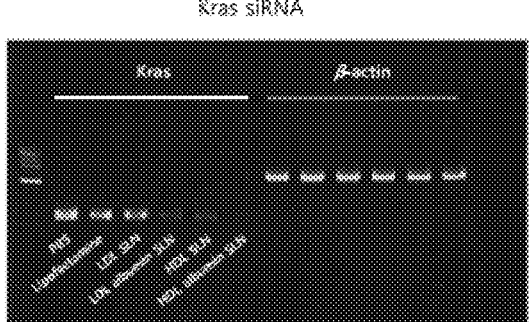 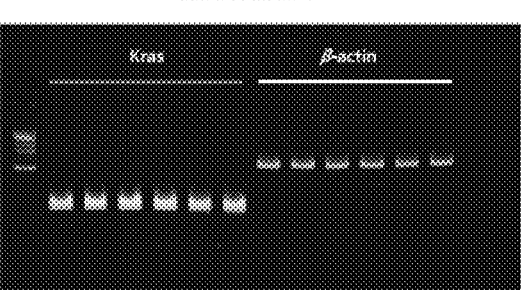
【Fig. 8】
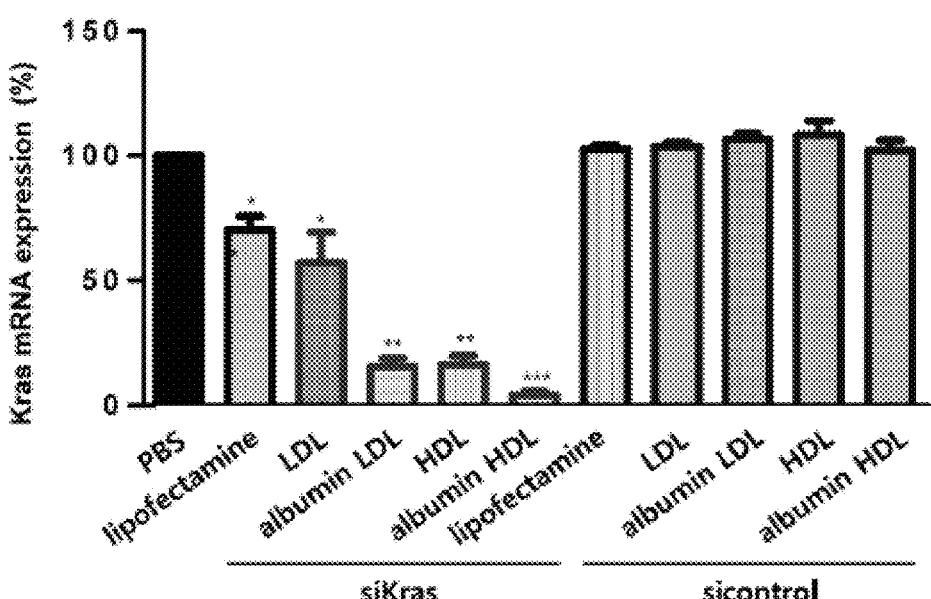
【Fig. 9】
Kras siRNA                control siRNA
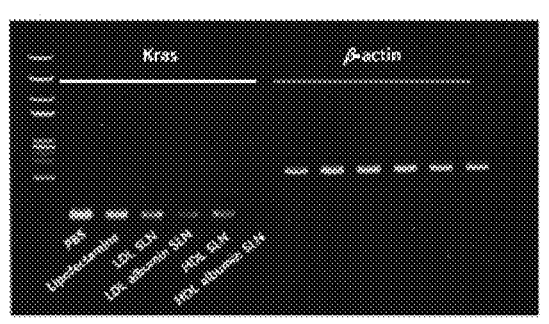 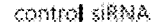 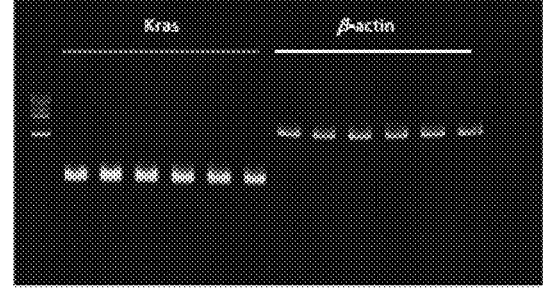

【Fig. 10】
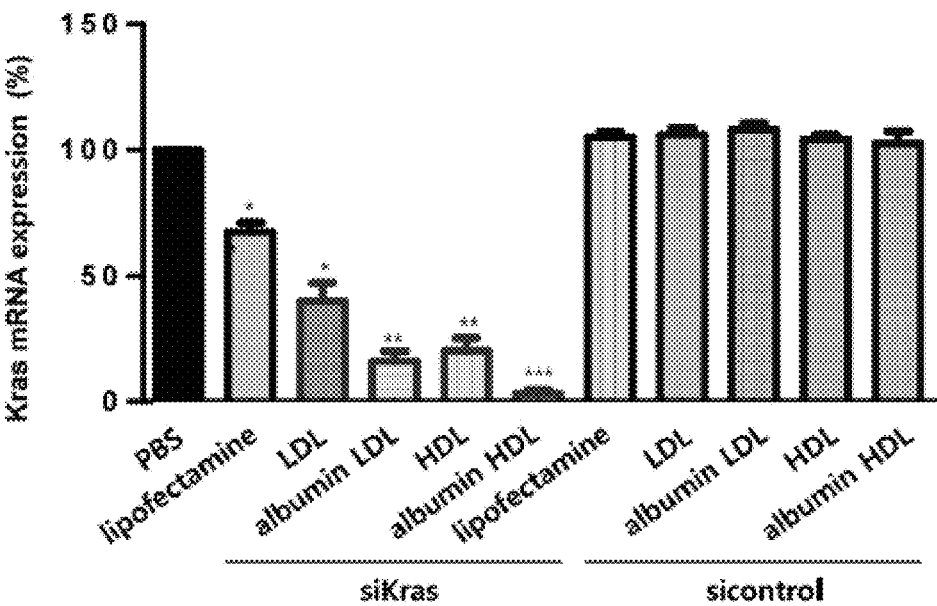
【Fig. 11】
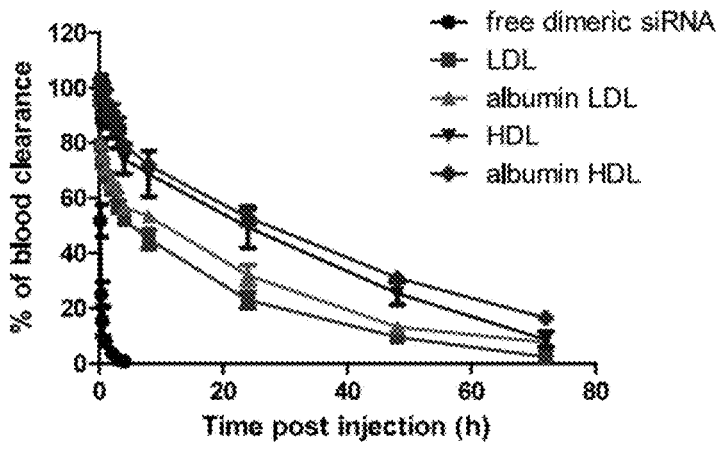
| Formulations | half life | early half life ( ~4h) | terminal half life (4~72h) |
|---|---|---|---|
| LDL | 14.8 | 5.4 | 15.4 |
| albumin LDL | 20.6 | 6.3 | 22.4 |
| HDL | 21.6 | 10.4 | 21.8 |
| albumin HDL | 28.4 | 10.8 | 30.3 |
| free dimeric siRNA | 1.1 | 0.7 | n.a. |

【Fig. 12】
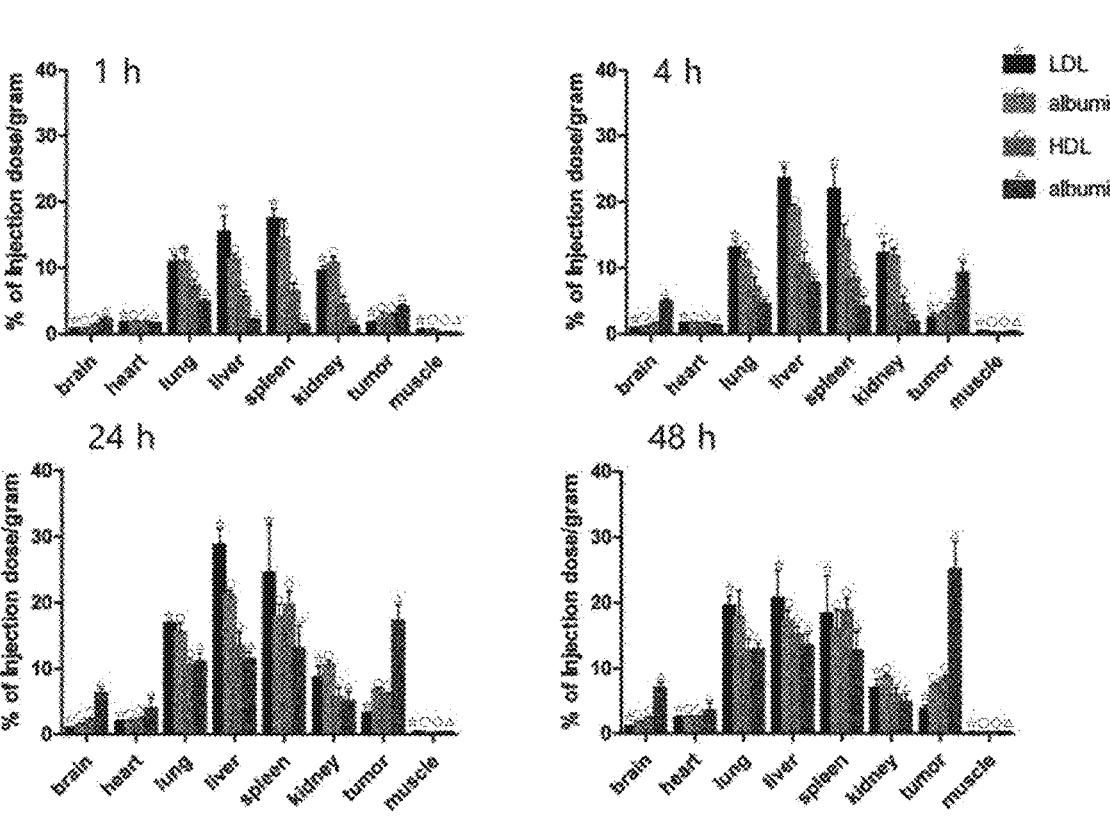

LIPOPROTEIN-MIMICKING SOLID LIPID NANOPARTICLES FOR DRUG DELIVERY AND USES THEREOF

SEQUENCE LISTING STATEMENT

A Sequence Listing conforming to the rules of WIPO Standard ST.25 is hereby incorporated by reference. Said Sequence Listing has been filed as an electronic document via EFS in ASCII formatted text. The electronic document, created on Aug. 5, 2023, is entitled "10820-030US1_ST25", and is 3,747 bytes in size.

TECHNICAL FIELD

The present invention relates to a lipoprotein-mimicking solid lipid nanoparticle for drug delivery and a use thereof as a drug carrier.

BACKGROUND ART

The K-ras gene (KRAS) is one of the ras genes that is commonly mutated in various cancer types, and mutations in codons 12 and 13 of the KRAS gene lead to functional alterations in the p21-ras protein, and as a result, are involved in carcinogenic processes by excessively transducing growth signals to the cell nucleus to promote the growth and division of cells. KRAS mutations appear in about 90% of pancreatic cancer cases, about 50% of colon cancer cases, and about 30% of non-small cell lung cancer cases, and thus are very commonly found in human cancer, and it was confirmed by mutation profiles that most of these mutations were clustered in codons 12 and 13 (Non-Patent Document 1).

Thus, although research has been attempted to develop anticancer drugs related to KRAS by various methods for several decades, KRAS has been considered as an undruggable target for therapeutic agents because there were no anticancer agents that led to clinical trials. KRAS is activated when it binds to guanosine triphosphate (GTP), but it has a very high binding force with GTP and has almost no pocket capable of binding to the surface, making it extremely difficult to develop new drugs targeting KRAS. Further, since KRAS is an intracellular protein, there is a problem in that an antibody with a large molecular weight cannot be used.

In addition, although nanoparticle paclitaxel, trade name Abraxane, which is a drug in which an anticancer agent paclitaxel is attached to albumin, appears to enhance the tumor response of paclitaxel by applying an albumin-fusion technique using various binding abilities, there is a problem in that the pharmacokinetics and biodistribution of Abraxane are less effective than those of Taxol formulations.

Therefore, there is a need for developing a drug carrier which is biocompatible, has high drug delivery efficiency, and also directly targets KRAS.

RELATED ART DOCUMENTS

Non-Patent Documents

1. Samowitz W S, et al., Cancer Epidemiol. Biomarkers Prev. 9: 1193-7, 2000

DISCLOSURE

Technical Problem

An object of the present invention is to provide a lipoprotein-mimicking solid lipid nanoparticle having excellent bioavailability and high efficiency drug delivery effects, and a use thereof as a drug carrier.

Technical Solution

The present inventors confirmed that when solid lipid nanoparticles with a composition similar to that of natural lipoproteins are prepared, they can be used as a drug carrier with high bioavailability while encapsulating a drug with high efficiency, thereby completing the present invention.

Therefore, the present invention relates to a biocompatible lipoprotein-mimicking solid lipid nanoparticle (SLN) for delivering a drug with high efficiency and a use thereof.

Advantageous Effects

According to the present invention, it is possible to prevent interparticle aggregation and secure structural stability by preparing core-shell structured lipoprotein-mimicking solid lipid nanoparticles consisting of a cholesteryl ester, a triglyceride, albumin-conjugated cholesterol, a fusogenic lipid and a cationic lipid. Furthermore, it is possible to provide a drug carrier with excellent bioavailability and improved drug encapsulation efficiency.

DESCRIPTION OF DRAWINGS

FIG. 1 schematically illustrates the preparation of lipoprotein-mimicking solid lipid nanoparticles according to the present invention and the morphology thereof as a drug carrier.

FIG. 2 illustrates the Z-average values of the lipoprotein-mimicking solid lipid nanoparticles according to the content of the constituent components of lipoprotein-mimicking solid lipid nanoparticles.

FIGS. 3A and 3B illustrate TEM photographs of lipoprotein-mimicking solid lipid nanoparticles.

FIG. 4 schematically illustrates the process of synthesizing monomeric siRNA into reducible dimeric siRNA.

FIG. 5 shows the results of confirming the reducibility of the reducible dimer siRNA.

FIG. 6 shows the results of confirming the intracellular uptake of siRNA/SLN complexes by flow cytometry.

FIG. 7 shows the results of confirming Kras mRNA levels by reverse transcriptase-polymerase chain reaction (RT-PCR) to confirm the gene silencing effects of siRNA/SLN complexes.

FIG. 8 shows the results of quantifying Kras mRNA levels to confirm the gene silencing effects of siRNA/SLN complexes.

FIG. 9 shows the results of confirming Kras mRNA levels by reverse transcriptase-polymerase chain reaction (RT-PCR) to confirm the gene silencing effects of siRNA/SLN complexes in an animal model.

FIG. 10 shows the results of quantifying Kras mRNA levels to confirm the gene silencing effects of siRNA/SLN complexes in an animal model.

FIG. 11 shows the results of confirming the blood clearances of siRNA/SLN complexes formed by dimeric siRNA in a mouse model.

FIG. 12 shows the results of confirming the biodistributions of siRNA/SLN complexes formed by dimeric siRNA in a mouse model.

MODES OF THE INVENTION

Hereinafter, the configuration of the present invention will be specifically described.

In the present invention, the numerical limitations indicate "or more" or "or less" unless otherwise specified.

The present invention provides low-density lipoprotein-mimicking solid lipid nanoparticles including: a core including a cholesteryl ester and a triglyceride; and a shell including an albumin-conjugated cholesterol, a fusogenic lipid and a cationic lipid.

In the present invention, a solid lipid nanoparticle (SLN) has a nanometer (nm) unit size in terms of morphology, and means a particle present in a solid matrix form, unlike liposome and emulsion formulations. The solid lipid nanoparticles of the present invention have a core-shell structure, and may be configured, for example, in a form that structurally traps a water-insoluble drug and/or nucleic acid in the central portion (core) or the surface portion (shell). The solid lipid nanoparticles according to the present invention may greatly increase the in vivo delivery efficiency of a water-insoluble drug and/or nucleic acid by capturing the water-insoluble drug and/or nucleic acid. The solid lipid nanoparticles may be prepared by a typical method, and may be performed by appropriately modifying the method, if necessary.

Natural high-density lipoproteins (HDLs) have a size of 5 to 17 nm, have the largest protein composition among lipoproteins, and thus have the highest density of 1.063 to 1.21 g/dL. For high-density lipoproteins, proteins account for about 50% of the total components, cholesterols about 17%, and phospholipids about 22%. The major proteins are apoA-I and apoA-II. The high-density lipoprotein structurally consists of two lipid phases (phospholipids, apolipoproteins and free cholesterols) and non-polar lipid phases (cholesteryl esters and triglycerides). Phospholipids have an advantage in that the surface of nanoparticles can be stabilized by emulsifying non-polar lipids.

The solid lipid nanoparticles according to the present invention are high-density lipoprotein (HDL)-mimicking solid lipid nanoparticles (SLNs). Unlike natural high-density lipoproteins, high-density lipoprotein-mimicking solid lipid nanoparticles according to the present invention may be substantially free of apolipoproteins. Further, unlike natural high-density lipoproteins including apolipoproteins, the high-density lipoprotein-mimicking solid lipid nanoparticles according to the present invention may include a high content of cationic lipids instead of apolipoproteins. By imparting cationicity to the surface of solid lipid nanoparticles by the cationic lipids, they may be bound to drugs and used as a drug carrier.

In addition, the high-density lipoprotein-mimicking solid lipid nanoparticles of the present invention may include in the form of albumin-conjugated cholesterol instead of free cholesterol, unlike natural high-density lipoproteins. By including albumin-conjugated cholesterol as described above, the solid lipid nanoparticles may have cancer cell targeting ability when used as a drug carrier. This cancer cell targeting ability is due to albumin conjugated with cholesterol, and in order to exhibit the cancer cell targeting ability by albumin, the particle size needs to be at a level that allows the particles to pass through the cell membrane, that is, at a level of 20 to 50 nm. Thus, the high-density lipoprotein-mimicking solid lipid nanoparticles may have a size of 20 to 50 nm.

Meanwhile, natural low-density lipoproteins (LDLs) consist of two lipid phases, that is, polar components (phospholipids and apolipoproteins) and non-polar neutral lipids consisting of cholesterol esters and triglycerides in advance, and have a size of about 18 to 25 nm and a zeta potential of −11.4±1.9 mV. Specifically, the core consists of 45% cholesterol ester and 3% triglyceride, and the surface consists of 10% cholesterol, 22% phospholipid and 20% apolipoprotein B-100.

The solid lipid nanoparticles according to the present invention are low-density lipoprotein (LDL)-mimicking solid lipid nanoparticles (SLNs). Unlike natural low-density lipoproteins, low-density lipoprotein-mimicking solid lipid nanoparticles according to the present invention may be substantially free of apolipoproteins. In addition, unlike natural low-density lipoproteins including apolipoproteins, the low-density lipoprotein-mimicking solid lipid nanoparticles according to the present invention may include fusogenic lipids and cationic lipids instead of phospholipids and apolipoproteins. By imparting cationicity to the surface of solid lipid nanoparticles by the cationic lipids, they may be bound to drugs and used as a drug carrier.

Furthermore, the low-density lipoprotein-mimicking solid lipid nanoparticles of the present invention may include in the form of albumin-conjugated cholesterol instead of free cholesterol, unlike natural low-density lipoproteins.

By including albumin-conjugated cholesterol as described above, the low-density lipoprotein-mimicking solid lipid nanoparticles may have cancer cell targeting ability when used as a drug carrier. Further, it is possible to prevent interparticle aggregation and form structurally stable nanoparticles by emulsifying non-polar lipids to provide surface stability.

This cancer cell targeting ability and permeability are due to albumin conjugated with cholesterol, and in order to exhibit the cancer cell targeting ability by albumin, the particle size needs to be at a level that allows the particles to pass through the cell membrane. That is, due to the enhanced permeability and retention (EPR) effect, new blood vessels in tumor tissue are incomplete and a gap of about 200 nm is opened, and particles within a size of 200 nm can penetrate the tumor blood vessels without entering normal tissue (enhanced permeability), or leaked materials are likely to stay because the lymphatic system is not developed in tumor tissue. Thus, the solid lipid nanoparticles according to the present invention have a size of 60 to 200 nm, and may stably deliver drugs to cancer tissue and the like due to the EPR effect.

In the present invention, the high-density lipoprotein-mimicking solid lipid nanoparticles and/or low-density lipoprotein-mimicking solid lipid nanoparticles may be high-density and/or low-density lipoprotein-mimicking cationic solid lipid nanoparticles in the form of cationic solid lipid nanoparticles. The nanoparticles are reconstituted by mimicking the constituents of natural high-density and/or low-density lipoproteins, and nucleic acid therapeutic agents such as proteins, peptides, aptamers or siRNA have a very low absorption rate into the circulation system due to their physicochemical properties. In addition, since solid lipid nanoparticles are degraded by proteolytic enzymes, peptidases, or nucleases, removed through the reticuloendothelial system (RES), and the like, and then rapidly excreted through the kidneys, there is an advantage in that the in vivo stability and bioavailability are excellent and the drug can be encapsulated and delivered with high efficiency because drugs are encapsulated in natural high-density lipoprotein-mimicking nanoparticles in which the rapid excretion is improved to inhibit degradation by the enzymes, absorption into target organs or cells is promoted, degradation by the reticuloendothelial system (RES) is inhibited, the residence time in blood can be extended, and natural lipoproteins are mimicked in vivo.

In the following examples, it was confirmed that the lipoprotein-mimicking nanoparticles have an excellent drug encapsulation rate by preparing high-density lipoprotein-mimicking solid lipid nanoparticles and low-density lipoprotein-mimicking solid lipid nanoparticles. More specifically, it was confirmed that the average particle size was about 100 nm for the low-density lipoprotein-mimicking solid lipid nanoparticles and about 30 nm for the high-density lipoprotein-mimicking solid lipid nanoparticles, and the drug encapsulation rate was at a similar level.

In the present invention, the lipoprotein-mimicking solid lipid nanoparticles may be referred to as solid lipid nanoparticles. In addition, unless otherwise described, the disclosed content should be understood to be applied to both low-density and/or high-density lipoprotein-mimicking solid lipid nanoparticles.

In the present invention, the core of solid lipid nanoparticles may trap a drug through hydrophobic interaction of a water-insoluble drug and/or nucleic acid gene inside the core in a solid state at room temperature and body temperature. The core of the solid lipid nanoparticles includes a cholesteryl ester and a triglyceride.

The cholesteryl ester, which is one of the components forming the core of the nanoparticles, is a compound in which a saturated or unsaturated fatty acid having 10 to 24 carbon atoms is ester-bonded to cholesterol, and may be an ester of an unsaturated fatty acid having 16 to 18 carbon atoms, such as oleic acid. The solid lipid nanoparticles according to the present invention may include single or multiple type(s) of cholesteryl esters.

In one exemplary embodiment, the cholesteryl ester may be one or more selected from the group consisting of cholesteryl stearate, cholesteryl palmitate, cholesterol hydroxystearate and soybean sterol, or derivative thereof, and may be preferably cholesteryl oleate.

The cholesteryl ester may be present in an amount of 5 to 60 parts by weight based on 100 parts by weight of the total lipoprotein-mimicking solid lipid nanoparticles.

For example, when the lipoprotein-mimicking solid lipid nanoparticles are high-density lipoprotein-mimicking solid lipid nanoparticles, the cholesteryl ester may be included in an amount of 5 to 30 parts by weight, 10 to 25 parts by weight, or 15 to 20 parts by weight based on 100 parts by weight of high-density lipoprotein-mimicking solid lipid nanoparticles. When the cholesteryl ester constitutes the core of high-density lipoprotein-mimicking nanoparticles in the range described above, it is possible to prepare solid lipid nanoparticles having excellent intracellular drug delivery efficiency because the solid lipid nanoparticles can pass through cell membranes while encapsulating a large amount of the drug. Furthermore, solid lipid nanoparticles similar to natural high-density lipoproteins may be prepared by including cholesteryl ester in the above content.

Further, for example, when the lipoprotein-mimicking solid lipid nanoparticles are low-density lipoprotein-mimicking solid lipid nanoparticles, the cholesteryl ester may be included in an amount of 30 to 60 parts by weight, more than 30 parts by weight and 50 parts by weight or less, or 40 to 50 parts by weight based on 100 parts by weight of low-density lipoprotein-mimicking solid lipid nanoparticles. When the cholesteryl ester constitutes the core of low-density lipoprotein-mimicking nanoparticles in the range described above, it is possible to prepare low-density lipoprotein-mimicking solid lipid nanoparticles having excellent intracellular drug delivery efficiency because the low-density lipoprotein-mimicking solid lipid nanoparticles can pass through cell membranes while encapsulating a large amount of the drug. In addition, solid lipid nanoparticles similar to natural low-density lipoproteins may be prepared by including cholesteryl ester in the above content.

Furthermore, the triglyceride, which is one of the components constituting the core of the nanoparticles, may be a purified triglyceride having compositions of various fatty acids, or a vegetable oil containing a triglyceride consisting of a plurality of fatty acids as a main component. For example, the triglyceride may be an animal or vegetable oil, and may be one or more selected from the group consisting of soybean oil, olive oil, cottonseed oil, sesame oil, cod-liver oil, and the like, but is limited thereto. More specifically, the triglyceride may be a compound in which three molecules of saturated or unsaturated fatty acid having 10 to 24 carbon atoms are ester-bonded to one molecule of glycerol.

In one exemplary embodiment, the triglyceride may be one or more selected from the group consisting of triheptanoin, trimyristin, tripalmitin, tristearin, and trilinolein, or derivatives thereof, and may be preferably triolein.

The triglyceride may be included in an amount of 0.01 to 5 parts by weight, 0.05 to 3.5 parts by weight, 0.1 to 2.5 parts by weight, or 0.5 to 1.5 parts by weight based on 100 parts by weight of the total lipoprotein-mimicking solid lipid nanoparticles. When a triglyceride constitutes the core of lipoprotein-mimicking solid lipid nanoparticles in the range described above, the triglyceride may be hydrophobically bound to cholesteryl ester to form nanoparticles having a size capable of passing through cell membranes.

The cholesteryl ester and triglyceride may form the core of the lipoprotein-mimicking solid lipid nanoparticles through hydrophobic bonding.

In the present invention, the shell of solid lipid nanoparticles is bound to the upper surface of the core by hydrophobic interaction, and cationic lipids capable of electrostatic interaction with drugs, particularly water-insoluble drugs and/or nucleic acid genes are exposed to the shell. The nanoparticles according to the present invention may be bound to drugs, particularly water-insoluble drugs and/or nucleic acid genes by electrostatic interactions through the cationic lipids exposed to the shell as described above to form a complex, and drugs, particularly water-insoluble drugs and/or nucleic acid genes may be stably delivered into cells. Thus, the shell of the nanoparticles includes albumin-conjugated cholesterols, fusogenic lipids and cationic lipids.

In the present invention, the albumin-conjugated cholesterol is a hydrophobic moiety, and may be prepared by conjugating albumin, which is a hydrophilic protein, to cholesterol, which is a natural lipid. In particular, the present invention may firmly bind cholesterol and albumin by covalently binding albumin to cholesterol. Through this, it is possible to provide cholesterol-albumin in which albumin is firmly bound to cholesterol at a predetermined ratio, unlike complexes in which two components are simply mixed and non-specifically bound by interaction. In the present invention, the albumin-conjugated cholesterol may be used interchangeably with the term cholesterol-albumin.

The albumin-conjugated cholesterol of the present invention can be prepared by various methods known in the art. Although not limited thereto, in one exemplary embodiment of the present invention, the albumin-conjugated cholesterol may be formed by reacting cholesterol chloroformate and albumin. This may be a compound obtained by the reaction between the chloroformate group of cholesterol chloroformate and the amine group of albumin.

The albumin is one of the proteins that constitute the basic materials of cells, and is a protein having the smallest molecular weight among simple proteins present in the natural state. Albumin is a water-soluble protein that is commonly found in blood plasma, and may also bind to various ligands such as water, cations such as calcium, sodium, and potassium, fatty acids, hormones, bilirubin, and drugs to play a role in regulating and transmitting the colloidal osmotic pressure of the blood. In particular, binding between a drug and albumin also significantly contributes to the expression of efficacy of the drug. The albumin may be obtained in a substantial amount from egg white (ovalbumin), bovine serum or human serum, and may also be extracted from soybeans, milk and grains. Alternatively, recombinant albumin obtained from transformants prepared so as to express a polypeptide having the same amino acid sequence as naturally occurring albumin may also be used.

Further, the cholesterol is a kind of sterol which is a combination of a steroid and an alcohol, is a lipid present in the cell membranes of all animal cells, and is an organic molecule carried through blood. Cholesterol is absorbed through food or synthesized in the body, is present at high concentrations in cell membrane-rich organs, and imparts appropriate membrane permeability and fluidity to cells. Because cholesterol includes a plurality of fused ring structures in the molecule, it can exhibit enhanced interactions with materials including ring structures.

As described above, the present invention may include albumin-conjugated cholesterol as a constituent component thereof, instead of free cholesterol which is a natural protein.

The albumin-conjugated cholesterol may be present in an amount of 1 to 20 parts by weight based on 100 parts by weight of the total solid lipid nanoparticles.

For example, when the lipoprotein-mimicking solid lipid nanoparticles are high-density lipoprotein-mimicking solid lipid nanoparticles, the albumin-conjugated cholesterol may be included in an amount of 1.5 to 8 parts by weight, 2 to 5 parts by weight, or 3.5 to 4.5 parts by weight based on 100 parts by weight of high-density lipoprotein-mimicking solid lipid nanoparticles. In addition, for example, when the lipoprotein-mimicking solid lipid nanoparticles are low-density lipoprotein-mimicking solid lipid nanoparticles, the albumin-conjugated cholesterol may be included in an amount of 3 to 15 parts by weight, 5 to 12 parts by weight, or 9 to 11 parts by weight based on 100 parts by weight of low-density lipoprotein-mimicking solid lipid nanoparticles. When albumin-conjugated cholesterol forms solid lipid nanoparticles in the range described above, it is possible to form solid lipid nanoparticles which prevents aggregation between particles and have an excellent drug encapsulation rate while mimicking natural lipoproteins. While encapsulating a large amount of the drug in the solid lipid nanoparticles as described above, the efficiency of delivering the drug to a target site may be maximized by preventing the nanoparticles from being degraded by phagocytosis. Furthermore, by including the albumin-conjugated cholesterol in the above content, the shell of the solid lipid nanoparticles may be firmly formed by the albumin-conjugated cholesterol, the efficiency of transfection of genetic traits for gene transfer may be improved, there is an advantage in that the cytotoxicity of cationic lipids to be described below is reduced, and phagocytosis may be suppressed to improve the drug delivery efficiency of solid lipid nanoparticles.

Albumin has endosomolytic activity capable of promoting the release of nanoparticles in the endosomal-lysosomal compartment, and thus may contribute to the improvement of drug delivery efficiency. For example, the following examples show that such endosomolytic activity contributes to the improvement of in vivo gene transfer (silencing) efficiency of a complex of solid lipid nanoparticles and siRNA (albumin_SLN/siRNA complex). Further, since the nanoparticles may maintain their nanostructures even during blood circulation, they are preferentially distributed in tumor tissues, so there is an advantage in that the therapeutic efficacy of the drug can be maximized while minimizing side effects.

The fusogenic lipids may be all types of neutral, cationic or anionic lipids capable of forming solid lipid nanoparticles, and may be a single phospholipid or a mixture of two or more phospholipids, but are not limited thereto. All types of fusogenic phospholipids may be used as the fusogenic lipid, and the fusogenic lipid may be one or more selected from the group consisting of, for example, 1,2-dioleoyl-sn-glycero-3-phosphatidylethanolamine (DOPE), palmitoyloleoylphosphatidylethanolamine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), distearoylphosphatidylethanolamine (DSPE), phosphatidylethanolamine (PE), dipalmitoylphosphatidylethanolamine, 1-palmitoyl-2-oleoyl-sn-glycero-3-phosphoethanolamine (POPE), 1-palmitoyl-2-oleoyl-sn-glycero-3-phosphocholine (POPC), 1,2-dioleoyl-sn-glycero-3-[phospho-L-serine] (DOPS), and 1,2-dioleoyl-sn-glycero-3-[phospho-L-serine], but is not limited thereto.

In one exemplary embodiment, the fusogenic lipid may be 1,2-dioleoyl-sn-glycero-3-phosphatidylethanolamine (DOPE).

The fusogenic lipid may be included in an amount of 5 to 40 parts by weight, 15 to 40 parts by weight, 20 to 35 parts by weight, or 20 to 30 parts by weight based on the total weight of the solid lipid nanoparticles. When the fusogenic lipid constitutes the solid lipid nanoparticles in the range described above, there is an advantage in that the efficiency of gene transfection is improved and the cytotoxicity of cationic lipids to be described below is reduced. In addition, fusogenic lipids help solid lipid nanoparticles to pass through cell membranes and endosomal escape, thereby facilitating intracellular drug delivery.

The cationic lipid may include cationic lipids that carry a net negative charge at a specific pH, such as physiological pH. For example, the cationic lipid may be one or more selected from the group consisting of 3-beta[N—(N',N'-dimethylaminoethane)carbamoyl]cholesterol (DC-cholesterol), 3-beta[N—(N',N',N'-trimethylaminoethane)carbamoyl]cholesterol (TC-cholesterol), 3-beta[N—(N'-monomethylaminoethane)carbamoyl]cholesterol (MC-cholesterol), 3-beta[N-(aminoethane)carbamolyl]cholesterol (AC-cholesterol), N—(N-aminoethane)carbamoylpropanoic tocopherol (AC-tocopherol), N—(N'-methylaminoethane)carbamoylpropanoic tocopherol (MC-tocopherol), N,N-dioleoyl-N,N-dimethylammonium chloride (DODAC), N,N-distearyl-N,N-dimethylammonium bromide (DDAB), N-(1-(2,3-dioleoyloxy)propyl-N,N, N-trimethylammonium chloride (DOTAP), N,N-dimethyl-(2,3-dioleoyloxy)propylamine (DODMA), N-(1-(2,3-dioleoyl)propyl)-N,N,N-trimethylammonium chloride (DOTMA), 1,2-dioleoyl-3-dimethylammonium-propane (DODAP), 1,2-dioleylcarbamyl-3-dimethylammonium-propane (DOCDAP), 1,2-dilineoyl-3-dimethylammonium propane (DLINDAP), dioleoyloxy-N-[2-sperminecarboxamido)ethyl}-N,N-dimethyl-1-propanaminium trifluoroacetate (DOSPA), dioctadecylamidoglycyl spermine (DOGS), 1,2-dimyristyloxypropyl-3-dimethyl-hydroxyethyl ammonium bromide (DMRIE), 3-dimethylamino-2-(cholest-5-en-3-beta-oxybutan-4-oxy)-1-(cis, cis- 9,12-octadecadienoxy)propane (CLinDMA), 2-[5'-(cholest-5-en-3-beta-oxy)-3'-oxapentoxy]-3-dimethyl-1-(cis, cis-9', 12'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-diacyl-3-trimethylammonium-propane (TAP), 1,2-diacyl-3-dimethylammonium-propane (DAP), 1,2-di-O-octadecenyl-3-trimethylammonium propane, and 1,2-dioleyl-3-trimethylammonium propane, but is not limited thereto.

In one exemplary embodiment, the cationic lipid may be 3-beta[N—(N',N'-dimethylaminoethane)carbamoyl]cholesterol (DC-cholesterol). DC-cholesterol is less toxic than other cationic lipids, and may be particularly desirable in that a DC-cholesterol-based gene carrier has been approved for use in the clinical treatment of various diseases such as melanoma, cystic fibrosis, cervical cancer, breast cancer or ovarian cancer The cationic lipid may be included in an amount of 10 to 60 parts by weight based on 100 parts by weight of the total solid lipid nanoparticles.

For example, when the lipoprotein-mimicking solid lipid nanoparticles are high-density lipoprotein-mimicking solid lipid nanoparticles, the cationic lipid may be included in an amount of 10 to 60 parts by weight, 35 to 58 parts by weight, or 40 to 50 parts by weight based on 100 parts by weight of high-density lipoprotein-mimicking solid lipid nanoparticles. When the cationic lipid constitutes the shell of the solid lipid nanoparticles in the content range described above, the solid lipid nanoparticles and are formed in a size capable of passing through cell membranes while encapsulating a large amount of the drug, and thus may efficiently deliver the drug.

Furthermore, for example, when the lipoprotein-mimicking solid lipid nanoparticles are low-density lipoprotein-mimicking solid lipid nanoparticles, the cationic lipid may be included in an amount of 10 to 40 parts by weight, 10 to 30 parts by weight, or 12 to 28 parts by weight based on 100 parts by weight of low-density lipoprotein-mimicking solid lipid nanoparticles. When the cationic lipid constitutes the shell of the solid lipid nanoparticles in the content range described above, the solid lipid nanoparticles and are formed in a size capable of passing through cell membranes while encapsulating a large amount of the drug, and thus may efficiently deliver the drug.

In the present invention, the shell may include albumin-conjugated cholesterol such that albumin is exposed at the surface of the shell, thereby maximizing intracellular drug delivery efficiency. Further, the shell may be substantially free of apolipoproteins. The solid lipid nanoparticles according to the present invention may include the cationic lipid as a constituent of the solid lipid nanoparticles instead of apolipoproteins, unlike solid lipid nanoparticles in the related art, so that cationic characteristics are imparted to the surface portion (shell) of the solid lipid nanoparticles by the cationic lipid, and the solid lipid nanoparticles may be formed with a size capable of passing through cell membranes.

In the present invention, the "substantially free of" means being included in an amount of less than 3 parts by weight or less than 1 part by weight based on 100 parts by weight of the total solid lipid nanoparticles.

In addition, the solid lipid nanoparticles may have an average particle diameter of 20 to 200 nm so as to facilitate intracellular drug delivery.

For example, when the lipoprotein-mimicking solid lipid nanoparticles are high-density lipoprotein-mimicking solid lipid nanoparticles, the average particle diameter may be 20 to 50 nm, 20 to 45 nm, 25 to 40 nm, or 20 to 40 nm.

Furthermore, for example, when the lipoprotein-mimicking solid lipid nanoparticles are low-density lipoprotein-mimicking solid lipid nanoparticles, the average particle diameter may be 60 to 200 nm, 60 to 150 nm, 25 to 40 nm, or 20 to 40 nm.

The solid lipid nanoparticles may have a uniform particle size distribution. Solid lipid nanoparticles having the diameter in the range described above and the uniform particle size distribution may be usefully utilized for systemic drug delivery.

In the present invention, the high-density lipoprotein-mimicking solid lipid nanoparticles may include, based on 100 parts by weight of the total high-density lipoprotein-mimicking solid lipid nanoparticles, 5 to 30 parts by weight of the cholesteryl ester, 0.01 to 5 parts by weight of the triglyceride, 1 to 20 parts by weight of the albumin-conjugated cholesterol, 5 to 40 parts by weight of the fusogenic lipid and 10 to 60 parts by weight of the cationic lipid.

Further, in the present invention, the low-density lipoprotein-mimicking solid lipid nanoparticles may include, based on 100 parts by weight of the total low-density lipoprotein-mimicking solid lipid nanoparticles, 30 to 60 parts by weight of the cholesteryl ester, 0.01 to 5 parts by weight of the triglyceride, 1 to 20 parts by weight of the albumin-conjugated cholesterol, 5 to 40 parts by weight of the fusogenic lipid and 10 to 40 parts by weight of the cationic lipid.

In addition, the present invention provides a method for preparing the lipoprotein-mimicking solid lipid nanoparticles.

The preparation method includes preparing an aqueous dispersion in which lipoprotein-mimicking solid lipid nanoparticles are dispersed by mixing a cholesteryl ester, a triglyceride, albumin-conjugated cholesterol, a fusogenic lipid and a cationic lipid in an organic solvent.

Furthermore, the preparation method may further include preparing albumin-conjugated cholesterol; and/or purifying and concentrating the aqueous dispersion by performing dialysis.

In the preparation method, all the contents described above may be applied as they are to all the descriptions of the cholesteryl ester, triglyceride, albumin-conjugated cholesterol, fusogenic lipid, cationic lipid and lipoprotein-mimicking solid lipid nanoparticles.

More specifically, the preparation method may include:
i) preparing albumin-conjugated cholesterol;
ii) preparing an aqueous dispersion in which solid lipid nanoparticles are dispersed by mixing a cholesteryl ester, a triglyceride, albumin-conjugated cholesterol, a fusogenic lipid and a cationic lipid in an organic solvent; and
iii) dialyzing the aqueous dispersion with distilled water at predetermined time intervals for 12 to 36 hours, and then concentrating the dialysate.

Step i) may include: dissolving cholesterol chloroformate in an organic solvent and then dropping the solution into an albumin solution for reaction; and dialyzing the reaction solution with distilled water for 12 to 36 hours, followed by lyophilization. In this case, the cholesterol chloroformate and albumin may be used at a molar ratio of 1:1 to 5:1, but the molar ratio is not limited thereto.

In Step ii), the organic solvent may be selected from among dimethylformamide, tetrahydrofuran, a C1 to C4 lower alcohol, methylene chloride, chloroform, acetone, dimethyl sulfoxide, N-methylpyrrolidone, dioxane, ethyl acetate, methyl ethyl ketone, acetonitrile and a mixture thereof, but is not limited thereto. Since the organic solvent is completely removed during the preparing of the solid lipid nanoparticles, toxicity caused by the organic solvent may not be considered.

In one exemplary embodiment, the organic solvent in Step ii) may be a mixture of chloroform and methanol.

Further, in Step ii), in the process of mixing the cholesteryl ester, triglyceride, albumin-conjugated cholesterol, fusogenic lipid and cationic lipid in the organic solvent, a process of ultrasonicating and/or drying the mixture under reduced pressure may be further included.

The lipoprotein-mimicking solid lipid nanoparticles of the present invention may be used as a carrier for drugs such as various water-insoluble drugs and/or nucleic acid genes through electrostatic interactions with the cationic lipid exposed at the surface of the shell. Thus, the present invention provides a composition for delivering a drug, including the lipoprotein-mimicking solid lipid nanoparticles.

In the present invention, the drug may include a water-insoluble drug, a nucleic acid, or a water-insoluble drug and a nucleic acid at the same time.

In the present invention, the water-insoluble drug is a poorly soluble drug, an anionic peptide, a protein, a hyaluronic acid-peptide conjugate or a hyaluronic acid-protein conjugate, but is not limited thereto. The poorly soluble drug may be selected from paclitaxel, docetaxel, amphotericin, doxorubicin, nifedipine, propofol, diazepam, estradiol, cyclosporine, ritonavir, saquinavir, biphenyl dimethyl dicarboxylate, Coenzyme Q10, ursodeoxycholic acid, ilaprazole, imatinib, mesylate, acyclovir, allopurinol, amiodarone, azathioprine, benazepril, calcitriol, candesartan, eprosartan, carbidopa/levidopa, clarithromycin, clozapine, desmopressin acetate, diclofenac, enalapril, famotidine, felodipine, fenofibrate, fentanyl, fexofenadine, fosinopril, furosemide, glyburide, hyoscyamine, imipramine, itraconazole, levothyroxine, atorvastatin, lovastatin, meclizine, megesterol, mercaptopurine, metolazone, mometasone, nabumetaone, omeprazole, paroxetine, propafenone, quinapril, simvastatin, sirolimus, tacrolimus, tizanidine, fluvastatin, pitavastatin, pravastatin, rosuvastatin, epirubicin or a mixture thereof, but is not limited thereto.

In one exemplary embodiment, the water-insoluble drug may be a poorly soluble drug.

In the composition, the water-insoluble drug and/or nucleic acid and solid lipid nanoparticles may form a complex at a weight ratio of 1:1 to 1:10 or 1:3 to 1:8.

The complex may include a form in which a water-insoluble drug and/or nucleic acid are/is bound to the shell of solid lipid nanoparticles through interaction, or a water-insoluble drug and/or nucleic acid are/is trapped in the core.

The nucleic acid may be one or more selected from the group consisting of small interfering RNA (siRNA), ribosomal ribonucleic acid (rRNA), ribonucleic acid (RNA), deoxyribonucleic acid (DNA), complementary deoxyribonucleic acid (cDNA), an aptamer, messenger ribonucleic acid (mRNA), transfer ribonucleic acid (tRNA) and an antisense oligodeoxynucleotide (AS-ODN), but is not limited thereto.

In one exemplary embodiment, the nucleic acid may be siRNA.

Particularly, siRNA refers to double-stranded RNA (duplex RNA), or single stranded RNA that takes the form of a double strand in single stranded RNA. Binding between double strands is achieved through hydrogen bonding between nucleotides, and not all nucleotides in double strands should be complementarily bound perfectly. The length of siRNA may be about 15 to 60, about 15 to 50, about 15 to 40, about 15 to 30, 15 to 25, 16 to 25, 19 to 25, 20 to 25, or 20 to 23 nucleotides. The length of siRNA means the number of nucleotides on one side of double stranded RNA, that is, the number of base pairs, and for single stranded RNA, it means the length of a double strand in single stranded RNA. Further, siRNA may consist of various functional groups-introduced nucleotides in order to increase blood stability or weaken immune reactions.

Therefore, the siRNA of the present invention may include a non-modified or modified form from typical siRNA.

In addition, the present invention provides a method for delivering a water-insoluble drug and/or nucleic acid to target cells using the lipoprotein-mimicking solid lipid nanoparticles.

The method may include:
  i) forming a complex of a water-insoluble drug and/or nucleic acid and the lipoprotein-mimicking solid lipid nanoparticles; and
  ii) transfecting target cells with the complex.

In Step i), the complex is characterized by being formed by mixing the lipoprotein-mimicking solid lipid nanoparticles in the presence of a water-insoluble drug and/or nucleic acid in, for example, phosphate buffered saline (PBS) or demineralized water, and in this case, the PBS has a pH of 7.0 to 8.0 and may include NaCl, but is not limited thereto.

Furthermore, in Step i), the water-insoluble drug and/or nucleic acid and solid lipid nanoparticles may form a complex at a weight ratio of 1:1 to 1:10 or 1:3 to 1:8.

Further, the present invention provides a pharmaceutical composition for preventing or treating cancer induced by KRAS gene mutation, including the lipoprotein-mimicking solid lipid nanoparticles in which a water-insoluble drug or nucleic acid targeting KRAS is trapped.

In the pharmaceutical composition, the above-described contents may be applied as they are or mutatis mutandis to the water-insoluble drug, nucleic acid and high-density lipoprotein-mimicking solid lipid nanoparticles.

The cancer induced by the KRAS gene mutation may be, for example, non-small cell lung cancer, colorectal cancer or pancreatic cancer, but is not limited thereto.

In the pharmaceutical composition, the lipoprotein-mimicking solid lipid nanoparticles in which the water-insoluble drug or nucleic acid targeting KRAS is trapped may be in the form of a complex of the water-insoluble drug or nucleic acid and the high-density lipoprotein-mimicking solid lipid nanoparticles.

The water-insoluble drug included in the complex may be a poorly soluble drug.

In addition, the nucleic acid targeting KRAS included in the complex may be a reducible nucleic acid dimer.

The benefits and features of the present invention, and the methods of achieving the benefits and features will become apparent with reference to embodiments to be described below in detail. However, the present invention is not limited to the exemplary embodiments to be disclosed below, but may be implemented in various other forms, and the present exemplary embodiments are only provided for rendering the disclosure of the present invention complete and for fully representing the scope of the invention to a person with ordinary skill in the technical field to which the present invention pertains, and the present invention will be defined only by the scope of the claims.

MODE FOR INVENTION

Examples

FIG. 1 schematically illustrates the process of preparing lipoprotein-mimicking solid lipid nanoparticles and the morphology of the lipoprotein-mimicking solid lipid nanoparticles as a drug carrier.

[Preparation Example 1] Preparation of Albumin-Corrugated Cholesterol (Cholesterol-Albumin)

To prepare albumin-conjugated cholesterol, human serum albumin (HSA, Sigma-Aldrich, Germany) and cholesterol chloroformate (Sigma-Aldrich, Germany) were used.

First, 0.5 mmol of human serum albumin was dissolved in 2 mL of phosphate buffered saline (PBS, pH 8.0). 1.5 mmol of cholesterol chloroformate was dissolved in 1 mL of DMF, and this solution was dropped into the human serum albumin solution. In this case, cholesteryl chloroformate and human serum albumin were used in a molar ratio of 3:1. Thereafter, after a reaction with gentle shaking at room temperature overnight, the reaction solution was dialyzed against 3 L of distilled water using a dialysis tube with a molecular cutoff of 12000 g/mol for 3 hours, and distilled water was exchanged at 3 to 4 hour intervals for 24 hours. Thereafter, the product solution was lyophilized to prepare albumin-conjugated cholesterol (hereinafter referred to as cholesterol-albumin).

[Preparation Example 2] Preparation of High-Density Lipoprotein (HDL)-Mimicking Solid Lipid Nanoparticles (SLNs)

HDL-mimicking SLNs were prepared by partially modifying the solvent-emulsification method.

Cholesteryl oleate and triolein were used as core structure lipids, and DOPE, the cholesterol-albumin prepared in Preparation Example 1 and DC-cholesterol were used as surface (shell) structure lipids. The components in the following Tables 1 and 2 were dissolved in 2 mL of a mixture of chloroform/methanol (2:1, v/v). 10 mL of deionized water was added thereto, and the mixture was thoroughly vortexed. The suspension was sonicated using a Branson Sonifier (20 kHz, duty cycle=40, power control=3.5) for 5 minutes. The emulsified solution was transferred to a rotary evaporator, and the solvent was removed by evaporation at a temperature of 52° C. or higher, which is the melting point of cholesteryl oleate. Finally, the aqueous dispersion of HDL-mimicking SLNs was purified by overnight dialysis (MWCO: 5,000) and concentrated to a maximum of 5 mg particle/mL through vacuum evaporation.

TABLE 1

| | Constituent component (%) | Example 1-1 | Example 1-2 | Example 1-3 | Example 1-4 | Example 1-5 | Example 1-6 |
|---|---|---|---|---|---|---|---|
| Core | Cholesteryl oleate | 15 | 18 | 20 | 22.5 | 22.5 | 22.5 |
| | Triolein | 1 | 1 | 1 | 3 | 1.5 | 1.5 |
| Shell | DOPE | 28 | 28 | 28 | 14 | 14 | 7 |
| | Cholesterol_albumin | 3 | 4 | 5 | 10 | 10 | 10 |
| | DC-Chol | 50 | 40 | 30 | 28 | 28 | 28 |
| | Z-average (Z-Ave) (d · nm) | 40 | 36.7 ± 0.2 | 50.00 | 75.5 ± 0.06 | 75.04 ± 0.11 | 81.46 ± 0.18 |
| | Polydispersity index (PDI) | 0.21 | 0.279 | 0.2 | 0.191 | 0.198 | 0.207 |
| | Zeta-potential (ZP) (mV) | 85 | 66.3 | 65 | 88.25 ± 6.58 | 63.7 ± 3.82 | 77.75 ± 4.31 |

TABLE 2

| | Constituent component (%) | Example 1-7 | Example 1-8 | Example 1-9 | Example 1-10 | Example 1-11 | Example 1-12 |
|---|---|---|---|---|---|---|---|
| Core | Cholesteryl oleate | 22.5 | 22.5 | 22.5 | 22.5 | 22.5 | 22.5 |
| | Triolein | 1.5 | 3 | 3 | 3 | 3 | 1.5 |
| Shell | DOPE | 14 | 7 | 7 | 14 | 7 | 7 |
| | Cholesterol_albumin | 5 | 5 | 10 | 5 | 5 | 5 |
| | DC-Chol | 28 | 28 | 14 | 14 | 14 | 14 |
| | Z-average (Z-Ave) (d · nm) | 68.07 ± 0.18 | 73.13 ± 2.21 | 116.4 ± 0.85 | 100.95 ± 0.49 | 101.25 ± 0.21 | 86.89 ± 1.01 |
| | Polydispersity index (PDI) | 0.200 | 0.216 | 0.193 | 0.190 | 0.201 | 0.170 |
| | Zeta-potential (ZP) (mV) | 97 ± 7.07 | 85.85 ± 6.15 | 72.7 ± 0.99 | 84.5 ± 7.92 | 81.15 ± 2.47 | 88.7 ± 3.25 |

15

Further, the particle size and zeta potential values according to the compositions of the prepared HDL-mimicking SLNs (Examples 1-1 to 1-12) were compared.

In this case, as a negative comparison group, although prepared with the composition of Example 1-2, solid lipid nanoparticles (SLNs) prepared using cholesterol instead of cholesterol-albumin were used. The SLNs were used as an HDL negative comparison group in the following Experimental Examples 1 to 5.

As a result, as shown in Tables 1 and 2, the size of the HDL-mimicking SLNs tended to decrease as the amount of cholesteryl oleate and albumin-conjugated cholesterol (cholesterol-albumin) decreased. In addition, it was confirmed in FIG. 2 that the size of HDL-mimicking SLNs tended to decrease as the amount of DC-Chol increased.

From the results of FIG. 2, it can be confirmed that the Z-average value of HDL-mimicking SLNs tends to increase as the content of cholesteryl oleate and cholesterol (cholesterol-albumin) increases and the content of DC-Chol decreases.

Based on this, Example 1-2 was selected as the optimum composition of HDL-mimicking SLNs.

[Preparation Example 3] Preparation of Low-Density Lipoprotein (LDL)-Mimicking Solid Lipid Nanoparticles (SLNs)

LDL-mimicking SLNs were prepared in the same manner as in Preparation Example 2, except that the components and compositions in the following Tables 3 and 4 were used.

16

As a result, as shown in Tables 3 and 4, it can be confirmed that the size of the LDL-mimicking SLNs tends to decrease as the amount of cholesteryl oleate and albumin-conjugated cholesterol (cholesterol-albumin) decreases. In addition, it can be confirmed that the size of LDL-mimicking SLNs decreases as the amount of DC-Chol increases (FIG. 2).

From the results of FIG. 2, it can be confirmed that the Z-average value of LDL-mimicking SLNs tends to increase as the content of cholesterol oleate and cholesterol (cholesterol-albumin) increases and the content of DC-Chol decreases.

Based on this, Example 2-5 was selected as the optimum composition of LDL-mimicking SLNs.

[Experimental Example 1] Comparison of Drug Encapsulation Rates Between Optimal HDL-Mimicking SLNs and Optimal LDL-Mimicking SLNs The drug encapsulation rates of HDL-mimicking SLNs (composition of Example 1-2) and LDL-mimicking SLNs (composition of Example 2-5) consisting of the compositions shown in the following Tables 5 and 6 were compared.

TABLE 3

| | Constituent component (%) | Example 2-1 | Example 2-2 | Example 2-3 | Example 2-4 | Example 2-5 |
|---|---|---|---|---|---|---|
| Core | Cholesteryl oleate | 45 | 45 | 45 | 45 | 45 |
| | Triolein | 3 | 3 | 3 | 1.5 | 3 |
| Shell | DOPE | 14 | 7 | 14 | 7 | 22 |
| | Cholesterol-albumin | 10 | 10 | 5 | 5 | 10 |
| | DC-Chol | 28 | 28 | 28 | 28 | 20 |
| | Z-average (Z-Ave) (d · nm) | 68.27 ± 0.71 | 93.72 ± 0.10 | 85.36 ± 0.98 | 84.75 ± 0.24 | 101.2 ± 0.8 |
| | Polydispersity index (PDI) | 0.204 | 0.190 | 0.208 | 0.182 | 0.163 |
| | Zeta-potential (ZP) (mV) | 105.5 ± 2.12 | 42.3 ± 5.37 | 92.5 ± 6.51 | 32.6 ± 0.00 | 65.7 |

TABLE 4

| | Constituent component (%) | Example 2-6 | Example 2-7 | Example 2-8 | Example 2-9 | Example 2-10 |
|---|---|---|---|---|---|---|
| Core | Cholesteryl oleate | 45 | 45 | 45 | 45 | 45 |
| | Triolein | 1.5 | 1.5 | 1.5 | 3 | 1.5 |
| Shell | DOPE | 7 | 14 | 7 | 14 | 14 |
| | Cholesterol-albumin | 10 | 5 | 5 | 10 | 10 |
| | DC-Chol | 14 | 14 | 14 | 14 | 14 |
| | Z-average (Z-Ave) (d · nm) | 115.65 ± 0.78 | 108.85 ± 1.20 | 105.7 ± 1.13 | 116.1 ± 0.99 | 154.7 ± 1.27 |
| | Polydispersity index (PDI) | 0.169 | 0.148 | 0.166 | 0.174 | 0.166 |
| | Zeta-potential (ZP) (mV) | 80.15 ± 0.64 | 84.65 ± 4.74 | 81.5 ± 0.85 | 85.4 ± 1.41 | 73.1 ± 2.69 |

Further, the particle size and zeta potential values according to the compositions of the prepared LDL-mimicking SLNs (Examples 2-1 to 2-10) were compared.

In this case, as a negative comparison group, although prepared with the composition of Example 2-5, solid lipid nanoparticles (SLNs) prepared using cholesterol instead of cholesterol-albumin were used. The SLNs were used as an LDL negative comparison group in the following Experimental Examples 1 to 5.

TABLE 5

| | SLN (HDL-mimicking) | | |
|---|---|---|---|
| | Constituent component | Proportion (%) (w/w) | Content (mg) |
| Core (central portion) | Cholesteryl oleate | 18 | 4.75 |
| | Triglyceride | 1 | 0.26 |

TABLE 5-continued

| | SLN (HDL-mimicking) | | |
|---|---|---|---|
| | Constituent component | Proportion (%) (w/w) | Content (mg) |
| Shell (surface portion) | Cholesterol (cholesterol_albumin) | 4 | 1.05 |
| | DOPE | 28 | 7.39 |
| | DC-chol | 49 | 12.93 |

TABLE 6

| | SLN (LDL-mimicking) | | |
|---|---|---|---|
| | Constituent component | Proportion (%) (w/w) | Content (mg) |
| Core (central portion) | Cholesteryl oleate | 45 | 8.43 |
| | Triglyceride | 3 | 0.56 |
| Shell (surface portion) | Cholesterol (cholesterol_albumin) | 10 | 1.87 |
| | DOPE | 22 | 5.25 |
| | DC-chol | 20 | 10.5 |

TABLE 7

| Formulation type | Average diameter (nm) | Polydispersity Index | ζ-potential |
|---|---|---|---|
| LDL negative comparison group | 92.5 ± 1.6 | 0.187 | 69.0 |
| LDL-mimicking SLN | 101.2 ± 0.8 | 0.163 | 65.7 |
| HDL negative comparison group | 32.0 ± 0.3 | 0.276 | 70.7 |
| HDL-mimicking SLN | 36.7 ± 0.2 | 0.279 | 66.3 |

TABLE 8

| Particle formulation | Amount of protein (nmol/mg) |
|---|---|
| LDL negative comparison group | n.a |
| LDL-mimicking SLN | 7.29 ± 0.66 |
| HDL negative comparison group | n.a |
| HDL-mimicking SLN | 6.28 ± 0.13 |

As a result, as shown in Tables 7 and 8, it can be confirmed that both HDL-mimicking SLNs and LDL-mimicking SLNs have excellent drug encapsulation rates.

More specifically, in the case of LDL-mimicking SLNs, the average particle size of the nanoparticles was measured to be at least 2.5-fold larger than that of HDL-mimicking SLNs, but the drug encapsulation rate was found to be at a similar level. Through this, it can be confirmed that the HDL-mimicking SLNs have a better drug encapsulation effect.

Further, FIG. 3A illustrates TEM photographs of the LDL negative comparison group (left photograph) and the LDL-mimicking SLNs (right photograph) as SLNs having the composition of Table 5. In addition, FIG. 3B illustrates TEM photographs of the HDL negative comparison group (left photograph) and the HDL-mimicking SLNs (right photograph) as SLNs having the composition of Table 6. As illustrated in FIG. 3, it can be confirmed that the HDL-mimicking SLNs and LDL-mimicking SLNs according to the present invention are uniform nanoparticles having excellent dispersibility without aggregation between particles.

[Preparation Example 4] Preparation of Dimeric siRNA

1) Selection of Kras sIRNA

For Kras siRNA sequences, research was conducted by selecting three libraries. The three sequences have not been published, and although Kras itself is a natural gene, it is up to the researcher to choose which sequence among the entire base sequence that constitutes the Kras gene is used as a target sequence of siRNA. The present inventors used the sequences of the following Table 9. All double-stranded monomeric siRNAs used in the present experiment were purchased by commissioning Bioneer (Daejeon, Korea) to perform synthesis.

TABLE 9

| SEQ ID NO. | Name | Sequence (5'→3') |
|---|---|---|
| 1 | Kras siRNA_#1_sense | UGAAUUAGCUGUAUCGUC AAGG |
| 2 | Kras siRNA_#1_antisense | UUGACGAUACAGCUAAUU CAUA |
| 3 | Kras siRNA_#2_sense | ACUGUACUCCUCUUGACCU GCU |
| 4 | Kras siRNA_#2_antisense | CAGGUCAAGAGGAGUACA GUUA |
| 5 | Kras siRNA_#3_sense | UAUAAUGGUGAAUAUCUU CAAA |
| 6 | Kras siRNA_#3_antisense | UGAAGAUAUUCACCAUUA UAUA |
| 7 | Control siRNA_sense | UGUGGUAGCUAUACGGAU AdTdT |
| 8 | Control siRNA_antisense | UAUCCGUAUAGCUACCAC AdTdT |

2) Synthesis of siRNA Dimer

Double-stranded monomeric siRNA (anti-Kras, scrambled) modified with a thiol group at the 3'-end (sense) was used to synthesize reducible dimeric siRNA linked through a cleavable coupling agent.

Briefly, 50 nmol of double-stranded monomeric siRNA in 500 μl of diethylpyrocarbonate (DEPC)-treated deionized water (DW) was activated with 50 nmol of a cleavable coupling agent dithio-bis-maleidoethane (DTME, 15.6 μg) contained in dimethyl sulfoxide (molar concentration of siRNA:DTME was 1:1). 750 mM NaCl was added to the solution (optimal solution pH range, 6.5 to 7.5) to minimize charge repulsion between highly anionic double-stranded siRNAs. After overnight incubation at room temperature with gentle shaking, the produced dimeric siRNA was purified by dialysis (MWCO: 10 kDa) against DW overnight and concentrated to 1 nmol/μl by vacuum evaporation. The process of synthesizing monomeric siRNA into reducible dimeric siRNA is schematically illustrated in FIG. 4.

3) Dissociation of Dimeric siRNA

Since the dimeric siRNA previously synthesized in 2) acts in the form of a monomer in cells, the action of siRNA may be performed in cells only when the synthesized dimeric siRNA can be separated into monomeric siRNA again. Thus, an experiment was conducted to prove that it is a reducible dimeric siRNA using dithiothreitol (DTT), which is a reducing agent.

To confirm the cleavage of the disulfide bond for the dimeric siRNA, 100 nmol of a dimeric siRNA sample (100 µl) was incubated in 2 µmol of dithiothreitol (DTT, 100 µl) at room temperature overnight. The final pH of the solution was adjusted to 8.0 using 5 M NaOH. The produced cleaved dimeric siRNA was purified by dialysis (MWCO: 10 kDa) against DW overnight and concentrated up to 1 nmol/µl by vacuum evaporation.

In addition, non-coupling linked dimeric siRNAs with sequences for scrambled monomeric siRNAs were obtained from Bioneer (Daejeon, Korea).

All the resulting products, monomeric siRNA, dimeric siRNA linked through cleavable disulfide bonds, cleaved monomeric siRNA and unconjugated dimeric siRNA were analyzed by 10% polyacrylamide gel electrophoresis (PAGE).

As a result, as illustrated in FIG. 5, it could be confirmed that the dimeric siRNA was cleaved into monomeric siRNA.

[Preparation Example 5] Preparation of Complex of Dimeric siRNA and Lipoprotein-Mimicking SLN Complexes of monomeric, dimeric siRNAs linked through cleavable disulfide bonds and non-coupling linked dimeric siRNA were formed using lipoprotein-mimicking SLNs (Examples 1-2 and 2-5). Each siRNA (1.5 µg, 100 µmol) was complexed with solid lipid nanoparticles (SLNs) at a weight ratio of 6 (siRNA/SLN) for 10 minutes (siRNA/SLN complex).

To investigate the stability of the complex, heparin was added to the complexes at various weight ratios of heparin/siRNA (0, 1, 2, 5, 10, 20 and 50), and the complexes were additionally incubated at 37° C. for 30 minutes. After incubation, the amount of degraded siRNA was analyzed by 1% agarose gel electrophoresis.

To analyze serum stability, the complex was incubated in 50% v/v serum at 37° C. for predetermined times (0, 2, 4, 8, 12, 24 and 48 hours), the resulting sample was additionally treated with heparin (100 µg) and a DTT solution (100 mM), and then the released siRNA fraction was subjected to agarose gel electrophoresis.

The hydrodynamic diameter and surface γ-potential values of the siRNA/SLN complex were measured at a wavelength of 663 nm and a fixed scattering angle of 900 using a Zetasizer Nano Series Nano ZS (Malvern Instruments Ltd., Malvern, UK) equipped with a He—Ne laser beam. All samples were measured in triplicate at 25° C.

The morphology and size of the siRNA/SLN complex were observed by AFM (XE-100, Park Systems, Korea). For AFM analysis, after the siRNA/SLN complex was placed on a fresh mica surface and dried in air, images were recorded in a non-contact mode at an acquisition frequency of 312 kHz.

[Experimental Example 2] Confirmation of Intracellular Uptake of sIRNA/SLN Complex In order to confirm and compare the intracellular uptake of the siRNA/SLN complex prepared in Preparation Example 5, FITC-labeled siRNA was used for complexation, and intracellular uptake was analyzed using a flow cytometer (FACSCalibur, USA). In this case, an H441 cell line was used as cells.

In the case of FITC-labeled monomeric siRNA, monomeric siRNA was end-labeled by FITC at the 5'-end (sense) with a thiol group modification at the 3'-end (sense), as a sequence for the scrambled monomeric siRNA, and was commissioned to synthesize and the FITC-labeled monomeric siRNA was purchased by commissioning Bioneer (Daejeon, Korea) to perform synthesis. The FITC-labeled dimeric siRNA was synthesized as described in the Dimeric siRNA Synthesis section and analyzed by 10% PAGE.

Cells were inoculated in 6-well plates at a density of $2 \times 10^4$ cells per well for 24 hours and then each transfected with the dimeric siRNA/SLN complex at 37° C. for a predetermined time (30 minutes) (128 nM siRNA). Cell uptake was stopped by removing the culture medium, and the transfected cells were softly washed three times with PBS, and then dispersed in PBS. Cellular fluorescence was measured using the FACSCalibur flow cytometry system (BD Bioscience) and CellQuest software (PharMinutesgen).

The results are illustrated in FIG. 6. In FIG. 6, dimeric siRNA/albumin HDL indicates the case of using the HDL-mimicking SLNs according to Example 1-2, and dimeric siRNA/HDL indicates the case of using the HDL negative comparison group. Further, dimeric siRNA/albumin LDL indicates the case of using the LDL-mimicking SLNs according to Example 2-5, and dimeric siRNA/LDL indicates the case of using the LDL negative comparison group.

As a result, as illustrated in FIG. 6, dimeric siRNA/albumin HDL and dimeric siRNA/albumin LDL showed an excellent degree of intracellular uptake, and dimeric siRNA/albumin HDL showed the highest intracellular uptake degree.

Such data suggests that albumin-fused HDL-mimicking siRNA/SLN complexes are formed with a nanoparticle size of about 50 nm, and can be used as an effective drug carrier due to the best intracellular uptake.

[Experimental Example 3] Confirmation of In Vitro Activity of siRNA/SLN Complex

The gene-silencing effects of siRNA/SLN complexes formed by two types of dimeric siRNA, Kras (endogenous) and scrambled (control), were confirmed and compared.

First, after complexes with the lipoprotein-mimicking SLNs prepared in Examples 1-2 and 2-5 were formed, cells were treated with the complexes, and gene-silencing effects were confirmed by performing reverse transcriptase-polymerase chain reaction (RT-PCR) at the cellular level of Kras mRNA. In this case, an H441 cell line was used as cells.

Briefly, cells were seeded in 6-well plates at a density of $2 \times 10^4$ cells per well for 24 hours, and then transfected with dimeric siRNA/SLN complexes at various siRNA concentrations (n=3 per group). After the cells were cultured for 3 days, the cells were harvested and total RNA was isolated using the TRIzol reagent according to the manufacturer's protocol.

cDNA was synthesized using a High Capacity RNA-to-cDNA kit according to the manufacturer's protocol.

DNA amplification for a target gene (human Kras) and a control gene (human β-actin) was performed by a primer and Prime Taq Premix under thermocycling conditions of 1 cycle of 94° C. for 2 minutes; 30 cycles of 94° C. for 30 seconds, 57° C. for 30 seconds, 72° C. for 1 minute; and 1 cycle of 72° C. for 5 minutes.

As primer sequences, the sequences in the following Table 10 were used.

TABLE 10

| SEQ ID NO. | Name | Sequence (5'→3') |
|---|---|---|
| 9 | Human_Kras_Primer_F | AATTGTCCATCTACCATGG |
| 10 | Human_Kras_Primer_R | GAGGTCAGCTGAAGCAAATCCAA |
| 11 | Human_β-actin_Primer_F | CCCAAAGTTCACAATGTGGC |
| 12 | Human_β-actin_Primer_R | AGGGAGACCAAAAGCCTTCA |

PCR products were analyzed by 1% agarose gel electrophoresis, and the intensity of each band was quantified using the ImageJ program.

The results are illustrated in FIGS. 7 and 8. In FIGS. 7 and 8 (and FIGS. 9 to 12 to be described below), albumin HDL indicates the case of using the HDL-mimicking SLNs according to Example 1-2 (that is, using the HDL-mimicking siRNA/SLN complex), and HDL indicates the case of using the HDL negative comparison group. In addition, albumin LDL indicates the case of using the LDL-mimicking SLNs according to Example 2-5 (that is, using the LDL-mimicking siRNA/SLN complex), and LDL indicates the case of using the LDL negative comparison group.

As a result, as illustrated in FIGS. 7 and 8, it can be confirmed that the HDL-mimicking siRNA/SLN complex according to the present invention exhibits the best Kras silencing effect. Through this, it can be confirmed that the HDL-mimicking siRNA/SLN complex has an excellent drug delivery effect.

[Experimental Example 4] Confirmation of In Vivo Activity of siRNA/SLN Complex

1) Construction of Animal Model

To construct a xenograft mouse model, cancer cells ($5 \times 10^5$ cells) were injected subcutaneously into the flanks of female SPF BALB/C-nu mice (8 weeks old). Treatment was initiated when tumors reached an average volume of 50 to 100 $mm^3$.

To examine and compare the gene silencing effects of two monomeric or dimeric siRNAs, Kras (endogenous) and scrambled (control), a complex with the protein-mimicking SLNs prepared in Examples 1-2 and 2-5 was formed, and then administered intravenously into female C57BL/6 mice through tail vein injection, and the gene silencing effect of mouse Kras mRNA in tumor tissue was evaluated by RT-PCR.

Briefly, formulations were diluted in PBS at the siRNA concentration so as to be administered to each mouse. After 24 hours of treatment, tumor tissue was pulverized, and a tissue lysate was prepared with a homogenizer (Tissuelyser, QIAGEN, Germany). Total RNA was isolated using the TRIzol reagent exactly according to the manufacturer's protocol and Kras mRNA levels normalized to β-actin were measured.

In the case of RT-PCR, DNA amplification for a target gene (mouse Kras) and a control gene (mouse β-actin) was performed with primers and Prime Taq Premix under thermocycling conditions of 1 cycle of 94° C. for 2 minutes; 26 cycles of 94° C. for 30 seconds, 57° C. for 30 seconds, 72° C. for 1 minute; and 1 cycle of 72° C. for 5 minutes.

As primer sequences, the sequences in the following Table 11 were used.

TABLE 11

| SEQ ID NO. | Name | Sequence (5'→3') |
|---|---|---|
| 13 | mouse_Kras_Primer_F | TCCAACGATCATGGACTTCA |
| 14 | mouse_Kras_Primer_R | CAGGACTTGGAGGTCTTGGA |
| 15 | mouse_β-actin_Primer_F | TGTTACCAACTGGGACGACA |
| 16 | mouse_β-actin_Primer_R | AAGGAAGGCTGGAAAA |

PCR products were analyzed by 1% agarose gel electrophoresis, and the intensity of each band was quantified using the ImageJ program.

As can be seen from the results of FIGS. 9 and 10, it can be confirmed that the HDL-mimicking siRNA/SLN complex according to the present invention exhibits the best gene transfer effect even in animal models, similar to the previous results (FIGS. 7 and 8).

[Experimental Example 5] Confirmation of Tissue Distribution and Pharmacokinetic Profile of siRNA To confirm and compare the biodistribution and blood clearance of siRNA/SLN complexes formed by dimeric siRNAs in mice, 125I-labeled siRNAs were prepared using the Bolton-Hunter method, and used for conjugation.

First, for the synthesis of radio-labeled monomeric siRNA, the Bolton-Hunter reagent, N-succinimidyl-3-(4-hydroxyphenyl)propionate (SHPP), was dissolved in DMSO at a concentration of 10 mg/ml, and 10 μl of a 125I solution (1 mCi) was added to 10 μl of the SHPP solution. Chloramine-T was dissolved in PBS at a concentration of 10 mg/ml, and 50 μl of the chloramine-T solution was immediately added to 20 μl of the prepared SHPP/125I mixture while being vigorously mixed for 15 seconds for iodination of SHPP. After the iodinated SHPP solution was extracted with 1 mL of a benzene/DMF mixture (40:1, v/v), the organic phase was transferred to a clean tube. The organic solvent was removed by evaporation, and the dried iodinated SHPP was dissolved and reacted with 10 nmol of amine-functionalized monomeric siRNA (100 μl) at 4° C. for 2 hours to covalently bond an NHS group on iodinated SHPP and an amine group modified at the 5'-end of the monomeric siRNA. 125I-labeled monomeric siRNA was purified by overnight dialysis (MWCO: 5 kDa) (molar ratio of the NHS group, the NHS group of SHPP/the amine group of monomeric siRNA).

In the case of amine-functionalized monomeric siRNA, monomeric siRNA was end-labeled by an amine group at the 5'-end (sense) with a thiol group modification at the 3'-end (sense) having a sequence for the scrambled siRNA, and the amine-functionalized monomeric siRNA was purchased by commissioning Bioneer (Daejeon, Korea) to perform synthesis. The 125I-labeled dimeric siRNA was synthesized as described in the Dimeric siRNA Synthesis section and analyzed by 10% PAGE.

A pharmacokinetic profile corrected for radioactive decay up to the time point of injection were measured by collecting blood samples from a group of female SPC C57BU/6 mice. After intravenous (iv) injection of siRNA/SLN complexes formed by 125I-labeled monomeric or dimeric siRNAs, sampling was performed at designated times, and the radio-activity of the harvested samples was measured using a γ counter (1470 automatic gamma counter, Perkin Elmer, USA). The time points used for the experiment were 0.25, 0.5, 1, 2, 4, 24 and 48 hours, and about 2 µl of blood was collected from the mouse tail vein and stored in 8 µl of an EDTA solution to prevent blood clotting (n=3 for each group).

To evaluate siRNA tissue distribution in vivo, an siRNA/SLN complex formed by 125I-labeled dimeric siRNA was injected into female SPFC57BU/6 mice through intravenous (iv) injection. At specific time points (1, 4, 24 and 48 hours) after injection, mice (n=3 mice/time point) were sacrificed, and sample organs were harvested and weighed. In vivo siRNA tissue distribution was calculated relative to the radioactivity values at the first injection from the radioactivity values in each tissue measured using a 7-counter (% of injection dose/gram).

As a result, as illustrated in FIG. 11, it could be confirmed that among all the experimental groups, the HDL-mimicking siRNA/SLN complex (albumin HDL) showed the best blood stability, thus exhibiting the highest blood half-life, and accordingly, more siRNA was distributed in cancer tissue over time (FIG. 12). Through this, it was confirmed that the HDL-mimicking siRNA/SLN complex according to the present invention had the highest drug delivery efficiency to cancer tissue.

[Experimental Example 6] Preparation of Water-Insoluble Drug Carrier

1) Preparation of Lipoprotein-Mimicking SLNs Encapsulating Paclitaxel (Taxol) as Water-Insoluble Drug (SLNs Encapsulating Taxol)

As shown in the following Tables 12 and 13, the constituent components were dissolved in 2 mL of a chloroform:methanol (2:1) solution contained in a glass vial. 10 mL of distilled water was added to the glass vial and the resulting mixture was mixed by vortexing for 1 minute, and then the solution was sonicated in a Branson sonicator 450 (20 kHz, duty cycle=40, power control=3.5) for 3 minutes. The solution was transferred to a rotary evaporator, and the chloroform:methanol (2:1, v/v) solution, which is a solvent, was removed at a temperature equal to or higher than 60° C., which is the melting point of cholesteryl oleate. Purification was performed in distilled water overnight using a dialysis membrane with a molecular weight of cut-off (MWCO) of 5000, and a solid lipid nanoparticle solution encapsulating a purified water-insoluble drug (Taxol) was stored at 4° C. to prepare solid lipid nanoparticles encapsulating a water-insoluble drug (Taxol) (Taxol-containing SLNs).

Here, when HDL-mimicking SLNs were used, HDL-mimicking SLNs encapsulating Taxol was expressed, and when LDL-mimicking SLNs were used, LDL-mimicking SLNs encapsulating Taxol was expressed.

TABLE 12

| Classification | Constituent component | Content | Content ratio (%) |
|---|---|---|---|
| Surface lipid portion (Surface lipid) | DOPE | 5.2 | 16.6 |
| | Cholesterol | 1.8 | 5.7 |
| | DC-cholesterol | 10.5 | 33.4 |
| Core lipid portion (Core lipid) | Cholesterol oleate | 8.4 | 26.8 |
| | Triolein | 0.5 | 1.6 |
| Drug (Core) | Taxol (paclitaxel) | 5 | 15.9 |

TABLE 13

| Classification | Constituent component | Content | Content ratio (%) |
|---|---|---|---|
| Surface lipid portion (Surface lipid) | DOPE | 245 | 15.2 |
| | Cholesterol-albumin | 206.25 | 12.8 |
| | DC-cholesterol | 490 | 30.4 |
| Core lipid portion (Core lipid) | Cholesterol oleate | 618.75 | 38.4 |
| | Triolein | 41.25 | 2.6 |
| Drug (Core) | Taxol (paclitaxel) | 10 | 0.6 |

2) Confirmation of Physicochemical Properties of SLNs Encapsulating Taxol

The average size and zeta potential of the HDL-mimicking SLNs encapsulating Taxol and the LDL-mimicking SLNs encapsulating Taxol prepared in Experimental Example 6-1) were measured by a laser light scattering method, and measurements were made using a dynamic light scattering machine (DSL) (Zeta-Plus, Brookhaven Instruments, NY) equipped with a He—Ne laser with a wavelength of 632 nm and a detection angle of 90°. When the concentration of HDL-mimicking SLNs encapsulating Taxol and LDL-mimicking SLNs encapsulating Taxol dispersed in distilled water at 25° C. was 5 mg/ml, the size was measured three times, and high performance liquid chromatography (HPLC) was used to evaluate the content and encapsulation rate of the drug contained in the HDL-mimicking SLNs encapsulating Taxol and the LDL-mimicking SLNs encapsulating Taxol. Distilled water was removed by freeze drying a solution of the HDL-mimicking SLNs encapsulating Taxol and the LDL-mimicking SLNs encapsulating Taxol. After solid lipid nanoparticles encapsulating a freeze-dried water-insoluble drug (Taxol) were dispersed in 20 ml of methanol and completely dissolved, the water-insoluble drug was extracted through a filter (Millex SR 0.45 µm filter unit), and then the amount of encapsulated water-insoluble drug was analyzed using high performance liquid chromatography, and the results are shown in the following Tables 14 and 15. In this case, the amount of water-insoluble drug was quantitatively analyzed by comparison with a calibration curve according to the concentration of the drug, and the amount (%, w/w) and encapsulation rate (%) of the encapsulated water-insoluble drug were analyzed together using the following Equations 1 and 2.

$$\text{Drug content (\%, w/w)} = \frac{\text{Amount of drug measured (mg)}}{\substack{\text{Amount of drug} \\ \text{carrier prepared (mg)}}} \times 100 \qquad \text{[Mathematical Equation 1]}$$

$$\text{Encapsulation rate (\%)} = \frac{\text{Amount of drug measured (mg)}}{\substack{\text{Amount of drug used} \\ \text{for preparation (mg)}}} \times 100 \qquad \text{[Mathematical Equation 2]}$$

TABLE 14

| Size (nm) | Surface charge (mV) | Drug encapsulation efficiency (%) | Drug content (%, w/w) |
|---|---|---|---|
| 120.1 ± 2.4 | 76.1 ± 8.4 | 69 | 11 |

TABLE 15

| Size (nm) | Surface charge (mV) | Drug encapsulation efficiency (%) | Drug content (%, w/w) |
|---|---|---|---|
| 115.1 ± 2.4 | 76.1 ± 8.4 | 93.2 | 14.9 |

Table 14 shows the results for HDL-mimicking SLNs encapsulating Taxol and Table 15 shows the results for LDL-mimicking SLNs encapsulating Taxol.

As shown in Tables 14 and 15, it was confirmed that HDL-mimicking SLNs encapsulating Taxol and LDL-mimicking SLNs encapsulating Taxol had stable physicochemical properties in an aqueous solution.

More specifically, it was confirmed that the HDL-mimicking SLNs encapsulating Taxol encapsulated the drug with an efficiency of 11% (w/w) relative to the particle weight, and are HDL-mimicking SLNs encapsulating Taxol with a size of about 115 to 125 nm and a surface charge of about 65 to 85 mV.

Furthermore, it was confirmed that the LDL-mimicking SLNs encapsulating Taxol encapsulated the drug with an efficiency of 14.9% (w/w) relative to the particle weight, and are LDL-mimicking SLNs encapsulating Taxol with a size of about 100 to 130 nm and a surface charge of about 65 to 85 mV.

INDUSTRIAL APPLICABILITY

According to the present invention, it is possible to prevent interparticle aggregation and secure structural stability by preparing core-shell structured protein-mimicking solid lipid nanoparticles consisting of a cholesteryl ester, a triglyceride, albumin-conjugated cholesterol, a fusogenic lipid and a cationic lipid. Furthermore, it is possible to provide a drug carrier with excellent bioavailability and improved drug encapsulation efficiency

The invention claimed is:

1. A high-density lipoprotein (HDL)-mimicking solid lipid nanoparticle comprising:
   a core comprising a triglyceride and a cholesteryl ester; and
   a shell comprising albumin-conjugated cholesterol, a fusogenic lipid and a cationic lipid;
   wherein the albumin-conjugated cholesterol is a reaction product of cholesteryl chloroformate and albumin;
   wherein the shell is substantially free of apolipoproteins;
   wherein the HDL-mimicking solid lipid nanoparticle comprises, based on 100 parts by weight in total:

10 to 25 parts by weight of the cholesteryl ester,
0.01 to 5 parts by weight of the triglyceride,
1 to 20 parts by weight of the albumin-conjugated cholesterol,
5 to 40 parts by weight of the fusogenic lipid, and
10 to 60 parts by weight of the cationic lipid.

2. The HDL-mimicking solid lipid nanoparticle of claim 1, wherein the cholesteryl ester is a compound in which a saturated or unsaturated fatty acid having 10 to 24 carbon atoms is ester-bonded to cholesterol.

3. The HDL-mimicking solid lipid nanoparticle of claim 1, wherein the triglyceride is a compound in which three molecules of a saturated or unsaturated fatty acid having 10 to 24 carbon atoms are ester-bonded to one molecule of glycerol.

4. The HDL-mimicking solid lipid nanoparticle of claim 1, wherein the chloroformate group of the cholesteryl chloroformate and the amine group of the albumin are bound.

5. The HDL-mimicking solid lipid nanoparticle of claim 4, wherein a molar ratio of cholesteryl chloroformate and albumin in the albumin-conjugated cholesterol is 1:1 to 5:1.

6. The HDL-mimicking solid lipid nanoparticle of claim 1, wherein the fusogenic lipid is one or more selected from the group consisting of 1,2-dioleoyl-sn-glycero-3-phosphatidylethanolamine (DOPE), palmitoyloleoylphosphatidylethanolamine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), distearoylphosphatidylethanolamine (DSPE), phosphatidylethanolamine (PE), dipalmitoylphosphatidylethanolamine, 1-palmitoyl-2-oleoyl-sn-glycero-3-phosphoethanolamine (POPE), 1-palmitoyl-2-oleoyl-sn-glycero-3-phosphocholine (POPC), 1,2-dioleoyl-sn-glycero-3-[phospho-L-serine] (DOPS), and 1,2-dioleoyl-sn-glycero-3-[phospho-L-serine].

7. The HDL-mimicking solid lipid nanoparticle of claim 1, wherein the cationic lipid is one or more selected from the group consisting of 3-beta[N—(N',N'-dimethylaminoethane) carbamoyl]cholesterol (DC-cholesterol), 3-beta[N—(N',N',N'-trimethylaminoethane) carbamoyl]cholesterol (TC-cholesterol), 3-beta[N—(N'-monomethylaminoethane) carbamoyl]cholesterol (MC-cholesterol), 3-beta[N-(aminoethane) carbamolyl]cholesterol (AC-cholesterol), N—(N'-aminoethane) carbamoylpropanoic tocopherol (AC-tocopherol), N—(N'-methylaminoethane) carbamoylpropanoic tocopherol (MC-tocopherol), N,N-dioleoyl-N,N-dimethyl-ammonium chloride (DODAC), N,N-distearyl-N,N-dimethylammonium bromide (DDAB), N-(1-(2,3-dioleoyloxy) propyl-N,N,N-trimethylammonium chloride (DOTAP), N,N-dimethyl-(2,3-dioleoyloxy) propylamine (DODMA), N-(1-(2,3-dioleoyl) propyl)-N,N,N-trimethylammonium chloride (DOTMA), 1,2-dioleoyl-3-dimethylammonium-propane (DODAP), 1,2-dioleylcarbamyl-3-dimethylammonium-propane (DOCDAP), 1,2-dilineoyl-3-dimethylammonium propane (DLINDAP), dioleoyloxy-N-[2-sperminecarboxamido)ethyl}-N,N-dimethyl-1-propanaminium trifluoroacetate (DOSPA), dioctadecylamidoglycyl spermine (DOGS), 1,2-dimyristyloxypropyl-3-dimethyl-hydroxyethyl ammonium bromide (DMRIE), 3-dimethylamino-2-(cholest-5-en-3-beta-oxybutan-4-oxy)-1-(cis, cis-9,12-octadecadienoxy) propane (CLinDMA), 2-[5'-(cholest-5-en-3-beta-oxy)-3'-oxapentoxy]-3-dimethyl-1-(cis, cis-9',12'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-diacyl-3-trimethylammonium-propane (TAP), 1,2-diacyl-3-dimethylammonium-propane (DAP), 1,2-di-O-octadecenyl-3-trimethylammonium propane, and 1,2-dioleyl-3-trimethylammonium propane.

8. The HDL-mimicking solid lipid nanoparticle of claim 1, wherein the HDL-mimicking solid lipid nanoparticle has a diameter of 20 to 200 nm.

9. A method for preparing high-density lipoprotein (HDL)-mimicking solid lipid nanoparticles, the method comprising preparing an aqueous dispersion in which HDL-mimicking solid lipid nanoparticles are dispersed by mixing a cholesteryl ester, a triglyceride, albumin-conjugated cholesterol, a fusogenic lipid and a cationic lipid in an organic solvent;

wherein the shell is substantially free of apolipoproteins;

wherein the HDL-mimicking solid lipid nanoparticle comprises, based on 100 parts by weight in total:

10 to 25 parts by weight of the cholesteryl ester, 0.01 to 5 parts by weight of the triglyceride, 1 to 20 parts by weight of the albumin-conjugated cholesterol, 5 to 40 parts by weight of the fusogenic lipid, and 10 to 60 parts by weight of the cationic lipid.

10. The method of claim 9, further comprising purifying and concentrating the prepared aqueous dispersion by dialysis.

11. The method of claim 9, wherein the albumin-conjugated cholesterol is prepared by mixing cholesteryl chloroformate dissolved in an organic solvent with an aqueous albumin solution.

12. The method of claim 10, wherein a molar ratio of cholesteryl chloroformate and albumin in the albumin-conjugated cholesterol is 1:1 to 5:1.

13. The method of claim 9, wherein the organic solvent is selected from among dimethylformamide, tetrahydrofuran, a C1 to C4 lower alcohol, methylene chloride, chloroform, acetone, dimethyl sulfoxide, N-methylpyrrolidone, dioxane, ethyl acetate, methyl ethyl ketone, acetonitrile and a mixture thereof.

14. The method of claim 9, wherein the HDL-mimicking solid lipid nanoparticles each have a diameter of 20 to 200 nm.

15. A composition for delivering a drug, comprising the HDL-mimicking solid lipid nanoparticle of claim 1.

16. The composition of claim 15, wherein the drug comprises one or more of a nucleic acid and a water-insoluble drug.

17. The composition of claim 16, wherein the nucleic acid is one or more selected from the group consisting of siRNA, rRNA, RNA, DNA, cDNA, an aptamer, mRNA, tRNA and an antisense-oligodeoxynucleotide (AS-ODN), and the nucleic acid is bound to the cationic lipid of the HDL-mimicking solid lipid nanoparticle by electrostatic interaction.

18. The composition of claim 16, wherein the water-insoluble drug is a poorly soluble drug, an anionic peptide, a protein, a hyaluronic acid-peptide conjugate or a hyaluronic acid-protein conjugate.

19. A pharmaceutical composition for preventing or treating cancer induced by KRAS gene mutation, comprising one or more of a nucleic acid and a water-insoluble drug targeting KRAS; and the HDL-mimicking solid lipid nanoparticle of claim 1.

20. The composition of claim 19, wherein the nucleic acid targeting KRAS is a reducible nucleic acid dimer.

* * * * *

SEQUENCE LISTING

```
<160> NUMBER OF SEQ ID NOS: 16

<210> SEQ ID NO 1
<211> LENGTH: 22
<212> TYPE: RNA
<213> ORGANISM: Artificial Sequence
<220> FEATURE:
<223> OTHER INFORMATION: Description of sequence: siRNA

<400> SEQUENCE: 1
ugaauuagcu guaucgucaa gg                                          22

<210> SEQ ID NO 2
<211> LENGTH: 22
<212> TYPE: RNA
<213> ORGANISM: Artificial Sequence
<220> FEATURE:
<223> OTHER INFORMATION: Description of sequence: siRNA

<400> SEQUENCE: 2
uugacgauac agcuaauuca ua                                          22

<210> SEQ ID NO 3
<211> LENGTH: 22
<212> TYPE: RNA
<213> ORGANISM: Artificial Sequence
<220> FEATURE:
<223> OTHER INFORMATION: Description of sequence: siRNA

<400> SEQUENCE: 3 acguacucc ucuugaccug cu                                           22

<210> SEQ ID NO 4
<211> LENGTH: 22
<212> TYPE: RNA
<213> ORGANISM: Artificial Sequence
<220> FEATURE:
<223> OTHER INFORMATION: Description of sequence: siRNA

<400> SEQUENCE: 4
caggucaaga ggaguacagu ua                                          22

<210> SEQ ID NO 5
<211> LENGTH: 22
<212> TYPE: RNA
<213> ORGANISM: Artificial Sequence
```

-continued

```
<220> FEATURE:
<223> OTHER INFORMATION: Description of sequence: siRNA

<400> SEQUENCE: 5
uauaauggug aauaucuuca aa                                              22

<210> SEQ ID NO 6
<211> LENGTH: 22
<212> TYPE: RNA
<213> ORGANISM: Artificial Sequence
<220> FEATURE:
<223> OTHER INFORMATION: Description of sequence: siRNA

<400> SEQUENCE: 6
ugaagauauu caccauuaua ua                                              22

<210> SEQ ID NO 7
<211> LENGTH: 21
<212> TYPE: DNA
<213> ORGANISM: Artificial Sequence
<220> FEATURE:
<223> OTHER INFORMATION: Description of sequence: siRNA
<220> FEATURE:
<221> NAME/KEY: misc_feature
<222> LOCATION: (1)..(19)
<223> OTHER INFORMATION: backbone is RNA

<400> SEQUENCE: 7
ugugguagcu auacggauat t                                               21

<210> SEQ ID NO 8
<211> LENGTH: 21
<212> TYPE: DNA
<213> ORGANISM: Artificial Sequence
<220> FEATURE:
<223> OTHER INFORMATION: Description of sequence: siRNA

<400> SEQUENCE: 8
uauccguaua gcuaccacat t                                               21

<210> SEQ ID NO 9
<211> LENGTH: 19
<212> TYPE: DNA
<213> ORGANISM: Artificial Sequence
<220> FEATURE:
<223> OTHER INFORMATION: Description of sequence: Primer

<400> SEQUENCE: 9
aattgtccat ctaccatgg                                                  19

<210> SEQ ID NO 10
<211> LENGTH: 23
<212> TYPE: DNA
<213> ORGANISM: Artificial Sequence
<220> FEATURE:
<223> OTHER INFORMATION: Description of sequence: Primer

<400> SEQUENCE: 10
gaggtcagct gaagcaaatc caa                                             23

<210> SEQ ID NO 11
<211> LENGTH: 20
<212> TYPE: DNA
<213> ORGANISM: Artificial Sequence
<220> FEATURE:
<223> OTHER INFORMATION: Description of sequence: Primer
```

```
<400> SEQUENCE: 11
cccaaagttc acaatgtggc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of sequence: Primer

<400> SEQUENCE: 12
agggagacca aaagccttca                                              20

<210> SEQ ID NO 13
<211> LENGTH: 20
<212> TYPE: DNA
<213> ORGANISM: Artificial Sequence
<220> FEATURE:
<223> OTHER INFORMATION: Description of sequence: Primer

<400> SEQUENCE: 13
tccaacgatc atggacttca                                              20

<210> SEQ ID NO 14
<211> LENGTH: 20
<212> TYPE: DNA
<213> ORGANISM: Artificial Sequence
<220> FEATURE:
<223> OTHER INFORMATION: Description of sequence: Primer

<400> SEQUENCE: 14
caggacttgg aggtcttgga                                              20

<210> SEQ ID NO 15
<211> LENGTH: 20
<212> TYPE: DNA
<213> ORGANISM: Artificial Sequence
<220> FEATURE:
<223> OTHER INFORMATION: Description of sequence: Primer

<400> SEQUENCE: 15
tgttaccaac tgggacgaca                                              20

<210> SEQ ID NO 16
<211> LENGTH: 16
<212> TYPE: DNA
<213> ORGANISM: Artificial Sequence
<220> FEATURE:
<223> OTHER INFORMATION: Description of sequence: Primer

<400> SEQUENCE: 16
aaggaaggct ggaaaa                                                  16
```